(12) United States Patent
Siena et al.

(10) Patent No.: US 7,635,570 B2
(45) Date of Patent: Dec. 22, 2009

(54) EPIDERMAL GROWTH FACTOR RECEPTOR GENE COPY NUMBER

(76) Inventors: Salvatore Siena, Via Costanza 35, I-20146 Milan (IT); Mauro Moroni, Piazza dei Daini 4, 20126 Milan (IT); Alberto Bardelli, Via Guinicelli 11/4, I-10132 Turin (IT)

( * ) Notice: Subject to any disclaimer, the term of this patent is extended or adjusted under 35 U.S.C. 154(b) by 90 days.

(21) Appl. No.: 11/396,311

(22) Filed: Mar. 30, 2006

(65) Prior Publication Data
US 2007/0087394 A1 Apr. 19, 2007

Related U.S. Application Data

(60) Provisional application No. 60/667,827, filed on Apr. 1, 2005.

(51) Int. Cl.
*G01N 33/574* (2006.01)
(52) U.S. Cl. .......................................... 435/7.23; 435/6
(58) Field of Classification Search ........................ None
See application file for complete search history.

(56) References Cited

U.S. PATENT DOCUMENTS

2004/0132097 A1* 7/2004 Bacus et al. ................. 435/7.1

FOREIGN PATENT DOCUMENTS

| EP | 0 712 863 A1 | 5/1996 |
| WO | WO 2004/111273 A2 | 12/2004 |
| WO | WO 2005/117553 A2 | 12/2005 |
| WO | WO 2006/108627 * | 10/2006 |
| WO | WO 2007/001868 A1 | 1/2007 |

OTHER PUBLICATIONS

Sridhar, Lancet Oncology, 2003, 4:397-406.*
Humblet, Expert Opin Pharmacother, 2004, 1621-1633.*
Hirsch et al, J Clin Oncol, 2003, 3798-3807.*
Amann et al., "Aberrant epidermal growth factor receptor signaling and enhanced sensitivity to EGFR inhibitors in lung cancer," *Cancer Res.*, 65: 226-235 (2005).
Barber et al., "Somatic mutations of *EGFR* in colorectal cancers and glioblastomas," *N. Engl. J. Med*, 351:2883 (2004).
Eberhard et al., "Mutations in the epidermal growth factor receptor and in KRAS are predictive and prognostic indicators in patients with non-small-cell lung cancer treated with chemotherapy alone and in combination with erlotinib," *J. Clin. Oncol.*, 23:5900-5909 (2005).
Gandara et al., "Epidermal growth factor receptor tyrosine kinase inhibitors plus chemotherapy: case closed or is the jury still out?" *J. Clin. Oncol.*, 23:5856-5858 (2005).
Hirsch et al., "Biomarkers for prediction of sensitivity to EGFR inhibitors in non-small cell lung cancer," *Curr. Opin. Oncol.*, 17:118-122 (2005).
Hirsch et al., "Epidermal growth factor receptor in non-small-cell lung carcinomas: correlation between gene copy number and protein expression and impact on prognosis," *J. Clin. Oncol.*, 21: 3798-3807 (2003).

Hirsch et al., "Increased epidermal growth factor receptor gene copy number detected by fluorescence in situ hybridization associates with increased sensitivity to gefitinib in patients with bronchioloalveolar carcinoma subtypes: A southwest oncology group study," *J. Clin. Oncol.*, 23: 6838-6845 (2005).
Johns et al., "Novel monoclonal antibody specific for the DE2-7 epidermal growth factor receptor (EGFR) that also recognizes the EGFR expressed in cells containing amplification of the EGFR gene," *Int. J. Cancer*; 98: 398-408 (2002).
Kobayashi et al., "*EGFR* mutation and resistance of non-small-cell lung cancer to gefitinib," *N. Engl. J. Med.*, 352:786-792 (2005).
Lynch et al., "Activating mutations in the epidermal growth factor receptor underlying responsiveness of non-small-cell lung cancer to gefitinib," *N. Engl. J. Med.*, 350:2129-2139 (2004).
Lynch et al., "A phase II trial of cetuximab as therapy for recurrent non-small cell lung cancer (NSCLC)," *J. of Clin. Oncol., 2004 ASCO Ann. Meeting Proc.*, 22(14S):7084 (2004).
McIntyre et al., "Panitumumab. Oncolytic-Anti-EGFR human monoclonal antibody," *Drugs of the Future*, 29: 793-797 (2004).
Moroni et al., "Gene copy number for epidermal growth factor receptor (EGFR) and clinical response to antiEGFR treatment in colorectal cancer: a cohort study," *Lancet Oncol.* 6: 279-286 (2005).
Paez et al., "EGFR mutations in lung cancer: correlation with clinical response to gefitinib therapy," *Science*, 304: 1497-1500 (2004).
Pao et al., "EGF receptor gene mutations are common in lung cancers from "never smokers" and are associated with sensitivity of tumors to gefitinib and erlotinib," *PNAS*, 101: 13306-13311 (2004).
Stephens et al., "Intragenic ERBB2 kinase mutations in tumours," *Nature*, 431:525-526 (2004).
Takano et al., "Epidermal growth factor receptor gene mutations and increased copy numbers predict gefitinib sensitivity in patients with recurrent non-small-cell lung cancer," *J. Clin. Oncol.*, 23: 6829-6837 (2005).
Vogel et al., "Efficacy and safety of trastuzumab as a single agent in first-line treatment of HER2- overexpressing metastatic breast cancer," *J. Clin. Oncol.* 20: 719-726 (2002).
Wang et at, "Prevalence of somatic alterations in the colorectal cancer cell genome," *PNAS*, 99:3076-3080 (2002).
PCT Notification of the Transmittal of the International Search Report and the Written Opinion of the International Searching Authority, or the Declaration mailed Oct. 17, 2006; International Search Report, and the Written Opinion of the International Searching Authority, in Application No. PCT/US2006/012267.
Mukohara et al., "Differential effects of gefitinib and cetuximab on non-small-cell lung cancers bearing epidermal growth factor receptor mutations," *J. Natl. Cancer Inst.*, 97: 1185-1194 (2005).
PCT International Preliminary Report on Patentability and Written Opinion of the International Searching Authority, mailed Oct. 3, 2007, for International Application No. PCT/US2006/012267.
Allison, "Is personalized medicine finally arriving?" *Nat. Biotech.*, 26: 509-517 (2008).

(Continued)

*Primary Examiner*—Misook Yu
*Assistant Examiner*—Mark Halvorson
(74) *Attorney, Agent, or Firm*—Finnegan, Henderson, Farabow, Garrett & Dunner, L.L.P.

(57) ABSTRACT

Methods of predicting whether an anti-epidermal growth factor receptor ("EGFr")-specific binding agent treatment will be efficacious in treating cancer, and methods of treating patients with anti-EGFr-specific binding agents, are provided.

19 Claims, 2 Drawing Sheets

OTHER PUBLICATIONS

Amado et al., "Wild-type KRAS is required for Panitumumab efficacy in patients with metastatic colorectal cancer" *Journal of Clinical Oncology*, 26(10): 1626-1634 (2008).

Amler et al., "Predicting clinical benefit in non-small-cell lung cancer patients treated with epidermal growth factor tyrosine kinase inhibitors," *Cold Spring Harbor Symp. Quant.Biol.*, 70: 483-488 (2005).

Baselga et al., "Determinants of *RAS*istance to anti-epidermal growth factor receptor agents," *J. Clin. Oncol.*, 26: 1582-1584 (2008).

Benvenuti et al., "Oncogenic activation of the RAS/RAF signaling pathway impairs the response of metastatic colorectal cancers to anti-epidermal growth factor receptor antibody therapies," *Cancer Res.*, 67: 2643-2648 (2007).

Finocchiaro et al., "EGFR, HER2 and Kras as predictive factors for cetuximab sensitivity in colorectal cancer," *ASCO*, 2007 ASCO Annual Meeting, Abstract No. 4021 (2007).

Hecht et al., "Panitumumab (pmab) efficacy in patients (pts) with metastatic colorectal cancer (mCRC) with low or undetectable levels of epidermal growth factor receptor (EGFr): Final efficacy and *KRAS* analyses," *ASCO*, 2008 Gastrointestinal Cancers Symposium, Abtract No: 343 (2008).

Moroni et al. "Somatic mutation of EGFR catalytic domain and treatment with gefitinib in colorectal cancer," Letter to the Editor, *Ann. Onc.*, 16: 1848-1849 (2005).

Moroni et al., "EGFR FISH in colorectal cancer: what is the current reality?" *Lancet Oncol.*, 9: 402-403 (2008).

Moroni et al., "Controversial evaluation of EGFR protein and gene status in predicting response to anti-EGFR monoclonal antibodies in metastatic colorectal cancer: a case report and review of the literature," *Targ. Oncol.*, 3:127-130 (2008).

Pessino et al., "First-line sincgle-agent cetuximab in patients with advanced colorectal cancer," *Annals of Oncology*, 19:711-716 (2008).

Sartore-Bianchi et al., "Epidermal growth factor receptor gene copy number and clinical outcome of metastatic colorectal cancer treated with panitumumab," *J. Clin. Oncol.*, 25: 3238-3245 (2007).

Van Custem et al, "Open label phase III trial of Panitumumab plus best supportive care compared with best supportive care alone in patients with chemotherapy-refractory metastatic colorectal cancer," *Journal of Clinical Oncology*, 25(13): 1658-1664 (2007).

Office Action Mailed Apr. 2, 2008 in U.S. Appl. No. 11/548,386.

"Response to Office Action Mailed Apr. 2, 2008," filed on Oct. 2, 2008, in U.S. Appl. No. 11/548,386.

Office Action Mailed Apr. 11, 2008 in U.S. Appl. No. 10/600,129.

"Response to Office Action Mailed Apr. 11, 2008," filed on Oct. 13, 2008, in U.S. Appl. No. 10/600,129.

Invitation to Respond to Written Opinion in Singapore Patent Application No. 200716407-2, mailed Oct. 15, 2008.

* cited by examiner

EPIDERMAL GROWTH FACTOR RECEPTOR GENE COPY NUMBER

This application claims the benefit of U.S. Provisional Application 60/667,827, filed Apr. 1, 2005. U.S. Provisional Application 60/667,827 is incorporated by reference herein in its entirety for any purpose.

FIELD

The present application relates to methods of predicting whether an anti-epidermal growth factor receptor ("EGFr")-specific binding agent treatment will be efficacious in treating cancer, and methods of treating patients with anti-EGFr-specific binding agents. Methods of determining the efficacy of treatments are provided.

BACKGROUND

Certain applications of monoclonal antibodies in cancer therapy rely on the ability of the antibody to specifically deliver to the cancerous tissues cytotoxic effector functions such as immune-enhancing isotypes, toxins or drugs. An alternative approach is to utilize monoclonal antibodies to directly affect the survival of tumor cells by depriving them of essential extracellular proliferation signals, such as those mediated by growth factors through their cell receptors. One of the attractive targets in this approach is the epidermal growth factor receptor (EGFr), which binds EGF and transforming growth factor α (TGFα) (see, e.g., Ullrich et al., Cell 61:203-212, 1990; Baselga et al., Pharmacol. Ther. 64: 127-154,1994; Mendelsohn et al., in Biologic Therapy of Cancer 607-623, Philadelphia: J.B. Lippincott Co., 1995; Fan et al., Curr. Opin. Oncol. 10: 67-73,1998). Binding of EGF or TGFα to EGFr, a 170 kDa transmembrane cell surface glycoprotein, triggers a cascade of cellular biochemical events, including EGFr autophosphorylation and internalization, which culminates in cell proliferation (see, e.g., Ullrich et al., Cell 61:203-212, 1990).

Several observations implicate EGFr in supporting development and progression of human solid tumors. EGFr has been demonstrated to be overexpressed on many types of human solid tumors (see, e.g., Mendelsohn Cancer Cells 7:359 (1989), Mendelsohn Cancer Biology 1:339-344 (1990), Modjtahedi and Dean Int'l J. Oncology 4:277-296 (1994)). For example, EGFr overexpression has been observed in certain lung, breast, colon, gastric, brain, bladder, head and neck, ovarian, and prostate carcinomas (see, e.g., Modjtahedi and Dean Int'l J. Oncology 4:277-296 (1994)). Certain groups have reported that an increase in receptor levels is associated with a poor clinical prognosis (see, e.g., Baselga et al. Pharmacol. Ther. 64: 127-154,1994; Mendelsohn et al., Biologic Therapy of Cancer pp. 607-623, Philadelphia: J.B. Lippincott Co., 1995; Modjtahedi et al., Intl. J. of Oncology 4:277-296,1994; Gullick, Br. Medical Bulletin, 47:87-98,1991; Salomon et al., Crit. Rev. Oncol. Hematol. 19: 183-232,1995). Other studies, however, suggest that prognosis cannot be directly correlated to EGFr overexpression (see, e.g., Rusch et al. Clin. Cancer Res. 3:515-522, 1997; Pfeiffer et al., Br. J. Cancer 74:86-91, 1996; Fontanini et al., Clin. Cancer Res. 4:241-249,1998; Greatens et al., Am. J. Respir. Crit. Care. Med. 157:1093-1097,1998; D'Amico et al., J. Thorac. Cardiovasc. Surg. 117:736-743,1999; Pastorino et al., J. Clin. Oncol. 15:2858-2865,1997). Both epidermal growth factor (EGF) and transforming growth factor-alpha (TGF-α) have been demonstrated to bind to EGFr and to lead to cellular proliferation and tumor growth. In many cases, increased surface EGFr expression was accompanied by production of TGFα or EGF by tumor cells, suggesting the involvement of an autocrine growth control in the progression of those tumors (see, e.g., Baselga et al. Pharmacol. Ther. 64: 127-154,1994; Mendelsohn et al., Biologic Therapy of Cancer pp. 607-623, Philadelphia: J.B. Lippincott Co., 1995; Modjtahedi et al., Intl. J. of Oncology 4:277-296, 1994; Salomon et al., Crit. Rev. Oncol. Hematol. 19: 183-232, 1995).

Thus, certain groups have proposed that antibodies against EGF, TGF-α, and EGFr may be useful in the therapy of tumors expressing or overexpressing EGF-r (see, e.g., Mendelsohn Cancer Cells 7:359 (1989), Mendelsohn Cancer Biology 1:339-344 (1990), Modjtahedi and Dean Int'l J. Oncology 4:277-296 (1994), Tosi et al. Int'l J. Cancer 62:643-650 (1995)). Indeed, it has been demonstrated that anti-EGFr antibodies blocking EGF and TGF-α binding to the receptor appear to inhibit tumor cell proliferation. At the same time, however, anti-EGFr antibodies have not appeared to inhibit EGF and TGF-α independent cell growth (Modjtahedi and Dean Int'l J. Oncology 4:277-296 (1994)).

Monoclonal antibodies specific to the human EGFr, capable of neutralizing EGF and TGFα binding to tumor cells and of inhibiting ligand-mediated cell proliferation in vitro, have been generated from mice and rats (see, e.g., Baselga et al., Pharmacol. Ther. 64: 127-154,1994; Mendelsohn et al., in Biologic Therapy of Cancer 607-623, Philadelphia: J.B. Lippincott Co., 1995; Fan et al., Curr. Opin. Oncol. 10: 67-73, 1998; Modjtahedi et al., Intl. J. Oncology 4: 277-296,1994). Some of those antibodies, such as the mouse 108, 225 (see, e.g., Aboud-Pirak et al., J. Natl. Cancer Inst. 80: 1605-1611, 1988) and 528 (see, e.g., Baselga et al., Pharmacol. Ther. 64: 127-154, 1994; Mendelsohn et al., in Biologic Therapy of Cancer 607-623, Philadelphia: J.B. Lippincott Co., 1995) or the rat ICR16, ICR62 and ICR64 (see, e.g., Modjtajedi et al., Intl. J. Oncology 4: 277-296,1994; Modjtahedi et al., Br. J. Cancer 67:247-253, 1993; Modjtahedi et al., Br. J. Cancer 67: 254-261,1993) monoclonal antibodies, were evaluated extensively for their ability to affect tumor growth in xenograft mouse models. Most of the anti-EGFr monoclonal antibodies were efficacious in preventing tumor formation in athymic mice when administered with the human tumor cells (Baselga et al. Pharmacol. Ther. 64: 127-154,1994; Modjtahedi et al., Br. J. Cancer 67: 254-261,1993). When injected into mice bearing established human tumor xenografts, the mouse monoclonal antibodies 225 and 528 caused partial tumor regression and required the co-administration of chemotherapeutic agents, such as doxorubicin or cisplatin, for eradication of the tumors (Baselga et al. Pharmacol. Ther. 64: 127-154, 1994; Mendelsohn et al., in Biologic Therapy of Cancer 607-623, Philadelphia: J.B. Lippincott Co., 1995; Fan et al., Cancer Res. 53: 4637-4642, 1993; Baselga et al., J. Natl. Cancer Inst. 85: 1327-1333, 1993). A chimeric version of the 225 monoclonal antibody (C225), in which the mouse antibody variable regions are linked to human constant regions, exhibited an improved in vivo anti-tumor activity but only at high doses (see, e.g., Goldstein et al., Clinical Cancer Res. 1: 1311-1318,1995; Prewett et al., J. Immunother. Emphasis Tumor Immunol. 19: 419-427,1996). The rat ICR16, ICR62, and ICR64 antibodies caused regression of established tumors but not their complete eradication (Modjtahedi et al., Br. J. Cancer 67: 254-261,1993). These results established EGFr as a promising target for antibody therapy against EGFr-expressing solid tumors and led to human clinical trials with the C225 monoclonal antibody in multiple human solid cancers (see, e.g., Baselga et al. Pharmacol. Ther. 64: 127-154, 1994; Mendelsohn et al., Biologic Therapy of Cancer pp.

607-623, Philadelphia: J.B. Lippincott Co., 1995; Modjtahedi et al., Intl. J. of Oncology 4:277-296,1994).

Certain advances in the biological arts made it possible to produce a fully human anti-EGFr antibody. Using mice transgenic for human immunoglobulin genes (Xenomouse™ technology, Abgenix, Inc.), human antibodies specific for human EGFr were developed (see, e.g., Mendez, Nature Genetics, 15: 146-156,1997; Jakobovits, Advanced Drug Delivery Reviews, 31(1-2): 33-42,1998; Jakobovits, Expert Opinion on Investigational Drugs, 7(4): 607-614,1998; Yang et al., Crit. Rev. Oncol. Hematol. 38(1):17-23, 2001; WO98/24893; WO98/50433). One such antibody, panitumumab, a human IgG2 monoclonal antibody with an affinity of $5 \times 10^{-11}$ M for human EGFr, has been shown to block binding of EGF to the EGFr, to block receptor signaling, and to inhibit tumor cell activation and proliferation in vitro (see, e.g., WO98/50433; U.S. Pat. No. 6,235,883). Studies in athymic mice have demonstrated that panitumumab also has in vivo activity, not only preventing the formation of human epidermoid carcinoma A431 xenografts in athymic mice, but also eradicating already-established large A431 tumor xenografts (see, e.g., Yang et al., Crit. Rev. Oncol. Hematol. 38(1):17-23, 2001; Yang et al., Cancer Res. 59(6):1236-43, 1999). Panitumumab has been considered for the treatment of renal carcinoma, colorectal adenocarcinoma, prostate cancer, and non small cell squamous lung carcinoma, among other cancers (see, e.g., U.S. Patent Publication No. 2004/0033543), and clinical trials are underway with that antibody.

In certain cell types, the binding of growth factors, such as EGFr, prevents apoptosis by stimulation of phosphatidylinositol 3-kinase ("PI3K") and B-Raf. PI3K activation triggers a molecular cascade leading to the downregulation of the central pathways controlling programmed cell death (Yao, R., Science 267:2003-2006,1995). Members of the Raf family also have been identified as regulators of programmed cell death in mammals (Hunter, Cell 80:225-236,1995). In Raf knockouts, mice lacking B-Raf showed disturbances in cell survival, while mice lacking Raf-1 or A-Raf did not show such disturbances (see, e.g., Pritchard, Curr. Biol. 6:614-617, 1996; Wojnowski, Nat. Genet. 16:293-297,1997), indicating that B-Raf may possess specific functions in cell death regulation. Both PI3K and B-Raf are of interest in cell proliferation disorders, particularly cancer.

SUMMARY

In certain embodiments, a method of predicting whether an EGFr-specific binding agent treatment will be efficacious in treating an EGFr-related cancer in a subject is provided, comprising determining the EGFr gene copy number in a sample from the subject, wherein the presence of an increased EGFr gene copy number in the sample predicts that an EGFr-specific binding agent treatment will be efficacious in treating an EGFr-related cancer in the subject.

In certain embodiments, a method of treating a subject having an EGFr-related cancer is provided, comprising: (a) determining the EGFr gene copy number in a sample from the subject; (b) determining whether there is an increased EGFr gene copy number in the sample; and (c) if there is an increased EGFr gene copy number in the sample, administering to the subject a pharmaceutically effective amount of an EGFr-specific binding agent.

In certain embodiments, a method of determining the efficacy of a treatment in a patient is provided, comprising: (a) determining the EGFr gene copy number in a first sample obtained from a patient to obtain a first EGFr gene copy number level; (b) administering the treatment to the patient; (c) determining the EGFr gene copy number in a second sample from the patient at a time following administration of the treatment, thereby generating a second EGFr gene copy number level; and (d) comparing the first and second EGFr gene copy number levels, wherein a decrease in the EGFr gene copy number in the second EGFr gene copy number level relative to the first EGFr gene copy number level indicates that the treatment is effective in the patient.

BRIEF DESCRIPTION OF THE FIGURES

FIG. 1A shows the staining pattern of normal colorectal mucosal cells. FIG. 1B shows the staining pattern of tumor cells from patient 7. FIG. 1C shows the staining pattern of tumor cells from patient 4. FIG. 1D shows the staining pattern of tumor cells from patient 1.

DETAILED DESCRIPTION OF CERTAIN PREFERRED EMBODIMENTS

Figure 1:
FIGS. 1A-1D are images from dual-color FISH assay analyses as seen by fluorescent microscope, according to work described in Example 3. In all four figures, EGFr genes appear red and CEP7 sequences appear green.
Figure 1:
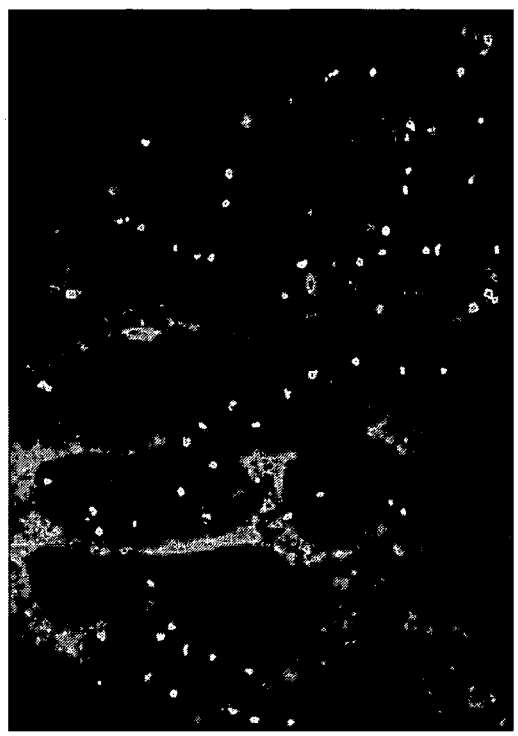
Figure 1:
Figure 1:
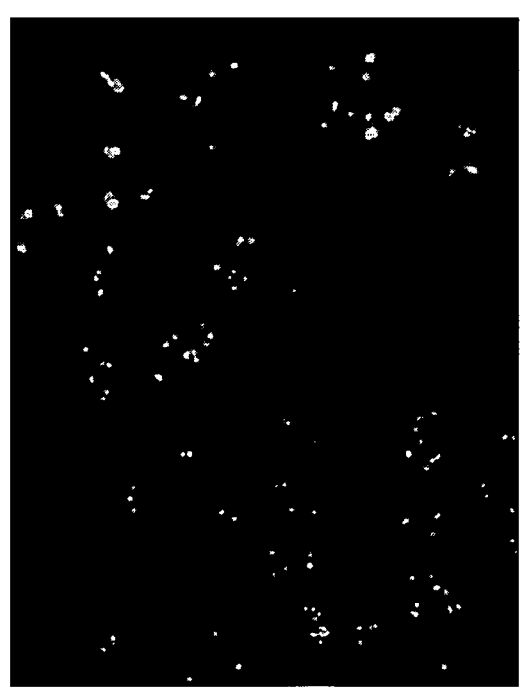

All references cited herein, including patents, patent applications, papers, textbooks, and the like, and the references cited therein, to the extent that they are not already, are hereby incorporated herein by reference in their entirety. The section headings used herein are for organizational purposes only and are not to be construed as limiting the subject matter described.

Definitions

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular.

Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to the manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. *Molecular Cloning: A Laboratory Manual* (2d ed., Cold Spring Harbor Laboratory Press, Cold Spring Harbor, N.Y. (1989)), which is incorporated herein by reference. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise.

As utilized in accordance with the present disclosure, the following terms, unless otherwise indicated, shall be understood to have the following meanings:

The terms "isolated polynucleotide" and "isolated nucleic acid" are used interchangeably, and as used herein shall mean a polynucleotide of genomic, cDNA, or synthetic origin or some combination thereof, which by virtue of its origin (1) is not associated with all or a portion of a polynucleotide in which the "isolated polynucleotide" is found in nature, (2) is operably linked to a polynucleotide which it is not linked to in nature, or (3) does not occur in nature as part of a larger sequence.

The terms "isolated protein" and "isolated polypeptide" are used interchangeably, and as referred to herein mean a protein of CDNA, recombinant RNA, or synthetic origin, or some combination thereof, which by virtue of its origin, or source of derivation, (1) is not associated with proteins found in nature, (2) is free of other proteins from the same source, e.g. free of murine proteins, (3) is expressed by a cell from a different species, or (4) does not occur in nature.

The terms "polypeptide" and "protein" are used interchangeably and are used herein as a generic term to refer to native protein, fragments, peptides, or analogs of a polypeptide sequence. Hence, native protein, fragments, and analogs are species of the polypeptide genus.

The term "EGFr polypeptide" encompasses native protein, as well as fragments, analogs, and mutants of a native protein. Thus, native EGFr protein, as well as fragments, analogs and mutants of native EGFr protein are species of the EGFr polypeptide genus.

The terminology "X#Y" in the context of a mutation in a polypeptide sequence is art-recognized, where "#" indicates the location of the mutation in terms of the amino acid number of the polypeptide, "X" indicates the amino acid found at that position in the wild-type amino acid sequence, and "Y" indicates the mutant amino acid at that position. For example, the notation "G13D" with reference to the Ras polypeptide indicates that there is a glycine at amino acid number 13 of the wild-type Ras sequence, and that glycine is replaced with a aspartic acid in the mutant Ras sequence.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

The term "operably linked" as used herein refers to the positioning of components such that they are in a relationship permitting them to function in their intended manner. A control sequence "operably linked" to a coding sequence is ligated in such a way that expression of the coding sequence is achieved under conditions compatible with the control sequences.

The term "control sequence" as used herein refers to polynucleotide sequences which are necessary to effect the expression and processing of coding sequences to which they are ligated. The nature of such control sequences differs depending upon the host organism; in prokaryotes, such control sequences generally include promoter, ribosomal binding site, and transcription termination sequences; in eukaryotes, generally, such control sequences include promoters and transcription termination sequences. The term "control sequences" is intended to include, at a minimum, all components whose presence is essential for expression and processing, and can also include additional components whose presence is advantageous, for example, leader sequences and fusion partner sequences.

The term "polynucleotide" as referred to herein means a polymeric form of nucleotides of at least 10 bases in length, either ribonucleotides or deoxynucleotides or a modified form of either type of nucleotide. The term includes single and double stranded forms of DNA.

The term "oligonucleotide" referred to herein includes naturally occurring and modified nucleotides linked together by naturally occurring, and non-naturally occurring oligonucleotide linkages. Oligonucleotides are a polynucleotide subset generally comprising a length of 200 bases or fewer. Preferably oligonucleotides are 10 to 60 bases in length and most preferably 12, 13, 14, 15, 16, 17, 18, 19, or 20 to 40 bases in length. Oligonucleotides are usually single stranded, e.g. for probes, although oligonucleotides may be double stranded, e.g. for use in the construction of a gene mutant. Oligonucleotides of the invention can be either sense or antisense oligonucleotides.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotide linkages such as phosphorothioate, phosphorodithioate, phosphoroselenoate, phosphorodiselenoate, phosphoroanilothioate, phoshoraniladate, phosphoroamidate, and the like. See e.g., LaPlanche et al. *Nucl. Acids Res.* 14:9081 (1986); Stec et al. *J. Am. Chem. Soc.* 106:6077 (1984); Stein et al. *Nucl. Acids Res.* 16:3209 (1988); Zon et al. *Anti-Cancer Drug Design* 6:539 (1991); Zon et al. *Oligonucleotides and Analogues: A Practical Approach*, pp. 87-108 (F. Eckstein, Ed., Oxford University Press, Oxford England (1991)); Stec et al. U.S. Pat. No. 5,151,510; Uhlmann and Peyman *Chemical Reviews* 90:543 (1990), the disclosures of which are hereby incorporated by reference. An oligonucleotide can include a label for detection, if desired.

The "copy number" of a nucleic acid refers to the number of discrete instances of that nucleic acid in a given sample. An "EGFr gene copy number" in a sample refers to the number of discrete copies of an EGFr gene in that sample. An "increased EGFr gene copy number" in a sample means that the number of discrete copies of the EGFr gene in a sample is increased from a reference. In certain such embodiments, the reference is another sample. In certain such embodiments, the reference is another sample taken from the same individual. In certain such embodiments, the reference is another sample taken from a different individual. In certain such embodiments, the reference is the EGFr gene copy number characteristic of a particular population.

The term "selectively hybridize" referred to herein means to detectably and specifically bind. Polynucleotides, oligonucleotides, and fragments thereof selectively hybridize to nucleic acid strands under hybridization and wash conditions that minimize appreciable amounts of detectable binding to nonspecific nucleic acids. High stringency conditions can be used to achieve selective hybridization conditions as known in the art and discussed herein. Generally, the nucleic acid sequence homology between polynucleotides, oligonucleotides, and fragments and a nucleic acid sequence of interest will be at least 80%, and more typically with preferably increasing homologies of at least 85%, 90%, 95%, 96%, 97%, 98%, 99%, and 100%. Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of more than 5 (in standard deviation units) using the program ALIGN with the mutation data matrix and a gap penalty of 6 or greater. See Dayhoff, M. O., in *Atlas of Protein Sequence and Structure*, pp. 101-110 (Volume 5, National Biomedical Research Foundation (1972)) and Supplement 2 to that volume, pp. 1-10. The two sequences or parts thereof are more preferably homologous if their amino acids are greater than or equal to 50% identical when optimally aligned using the ALIGN program. The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference nucleotide sequence "TATAC" and is complementary to a reference nucleotide sequence "GTATA".

The following terms are used to describe the sequence relationships between two or more polynucleotide or amino acid sequences: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing or may comprise a complete cDNA or gene sequence. Generally, a reference sequence is at least 18 nucleotides or 6 amino acids in length, frequently at least 24 nucleotides or 8 amino acids in length, and often at least 48 nucleotides or 16 amino acids in length. Since two polynucleotides or amino acid sequences may each (1) comprise a sequence (i.e., a portion of the complete polynucleotide or amino acid sequence) that is similar between the two molecules, and (2) may further comprise a sequence that is divergent between the two polynucleotides or amino acid sequences, sequence comparisons between two (or more) molecules are typically performed by comparing sequences of the two molecules over a "comparison window" to identify and compare local regions of sequence similarity. A "comparison window", as used herein, refers to a conceptual segment of at least 18 contiguous nucleotide positions or 6 amino acids wherein a polynucleotide sequence or amino acid sequence may be compared to a reference sequence of at least 18 contiguous nucleotides or 6 amino acid sequences and wherein the portion of the polynucleotide sequence in the comparison window may comprise additions, deletions, substitutions, and the like (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman *Adv. Appl. Math.* 2:482 (1981), by the homology alignment algorithm of Needleman and Wunsch *J. Mol. Biol.* 48:443 (1970), by the search for similarity method of Pearson and Lipman Proc. *Natl. Acad. Sci.* (*U.S.A.*) 85:2444 (1988), by computerized implementations of these algorithms (GAP, BESTFIT, FASTA, and TFASTA in the Wisconsin Genetics Software Package Release 7.0, (Genetics Computer Group, 575 Science Dr., Madison, Wis.), Geneworks, or MacVector software packages), or by inspection, and the best alignment (i.e., resulting in the highest percentage of homology over the comparison window) generated by the various methods is selected.

The term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally. aligned sequences over the window of comparison, determining the number of positions at which the identical nucleic acid base (e.g., A, T, C, G, U, or I) or residue occurs in both sequences to yield the number of matched positions, dividing the number of matched positions by the total number of positions in the comparison window (i.e., the window size), and multiplying the result by 100 to yield the percentage of sequence identity. The terms "substantial identity" as used herein denotes a characteristic of a polynucleotide or amino acid sequence, wherein the polynucleotide or amino acid comprises a sequence that has at least 85 percent sequence identity, preferably at least 90 to 95 percent sequence identity, more usually at least 96, 97, 98, or 99 percent sequence identity as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference.sequence to the sequence which may include deletions or additions which total 20 percent or less of the reference sequence over the comparison window. The reference sequence may be a subset of a larger sequence.

As used herein, the twenty conventional amino acids and their abbreviations follow conventional usage. See *Immunology—A Synthesis* ($2^{nd}$ Edition, E. S. Golub and D. R. Gren, Eds., Sinauer Associates, Sunderland, Mass. (1991)), which is incorporated herein by reference. The term "amino acid" or "amino acid residue," as used herein, refers to naturally occurring L amino acids or to D amino acids. The commonly used one- and three-letter abbreviations for amino acids are used herein (Bruce Alberts et al., *Molecular Biology of the Cell*, Garland Publishing, Inc., New York (4th ed. 2002)). Stereoisomers (e.g., D-amino acids) of the twenty conventional amino acids, unnatural amino acids such as α-,α-disubstituted amino acids, N-alkyl amino acids, lactic acid, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the lefthand direction is the amino terminal direction and the righthand direction is the carboxy-terminal direction, in accordance with standard usage and convention.

Similarly, unless specified otherwise, the lefthand end of single-stranded polynucleotide sequences is the 5' end; the lefthand direction of double-stranded polynucleotide sequences is referred to as the 5' direction. The direction of 5' to 3' addition of nascent RNA transcripts is referred to as the transcription direction. Sequence regions on the DNA strand having the same sequence as the RNA and which are 5' to the 5' end of the RNA transcript are referred to as "upstream sequences". Sequence regions on the DNA strand having the same sequence as the RNA and which are 3' to the 3' end of the RNA transcript are referred to as "downstream sequences".

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95, 96, 97, or 98 percent sequence identity, and most preferably at least 99 percent sequence identity. Preferably, residue positions which are not identical differ by conservative amino acid substitutions. As discussed herein, minor variations in the amino acid sequences of antibodies or immunoglobulin molecules are contemplated as being encompassed by the present invention, providing that the variations in the amino acid sequence maintain at least 75%, more preferably at least 80%, 90%, 95%, and most preferably 99%. Conservative amino acid substitutions are those that take place within a family of amino acids that are related in their side chains. Genetically encoded amino acids are generally divided into families: (1) acidic amino acids (e.g., aspartate and glutamate); (2) basic amino acids (e.g., lysine, arginine, and histidine); (3) non-polar amino acids (e.g., alanine, valine, leucine, isoleucine, proline, phenylalanine, methionine, and tryptophan); and (4) uncharged polar amino acids (e.g., glycine, asparagine, glutamine, cysteine, serine, threonine, and tyrosine). Other families of amino acids include, but are not limited to: serine and threonine are an aliphatic-hydroxy family; asparagine and glutamine are an amide-containing family; alanine, valine, leucine and isoleucine are an aliphatic family; phenylalanine, tryptophan, and tyrosine are an aromatic family, and cysteine and methionine as a sulfur-containing side chain family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Exemplary conservative amino acid substitution groups include, but are not limited to: valine-leucine-isoleucine, phenylalanine-tyrosine, lysine-arginine, alanine-valine, glutamic acid-aspartic acid, cysteine-methionine, and asparagine-glutamine.

Preferred amino acid substitutions are those which: (1) reduce susceptibility to proteolysis, (2) reduce susceptibility to oxidation, (3) alter binding affinity for forming protein complexes, (4) alter binding affinities, and (5) confer or modify other physicochemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in *Proteins, Structures and Molecular Principles* (Creighton, Ed., W. H. Freeman and Company, New York (1984)); *Introduction to Protein Structure* (C. Branden and J. Tooze, eds., Garland Publishing; New York, N.Y. (1991)); and Thornton et at. *Nature* 354:105 (1991), which are each incorporated herein by reference.

The term "analog" as used herein refers to polypeptides which are comprised of a segment of at least 25 amino acids that has substantial identity to a portion of an amino acid sequence of a naturally occurring polypeptide and which has at least one of the activities of the naturally occurring polypeptide. Typically, polypeptide analogs comprise a conservative amino acid substitution (or addition or deletion) with respect to the naturally-occurring sequence. Analogs typically are at least 20 amino acids long, preferably at least 50 amino acids long or longer, and can often be as long as a full-length naturally-occurring polypeptide.

Peptide analogs are commonly used in the pharmaceutical industry as non-peptide drugs with properties analogous to those of the template peptide. Those types of non-peptide compound are termed "peptide mimetics" or "peptidomimetics". Fauchere, *J. Adv. Drug Res.* 15:29 (1986); Veber and Freidinger *TINS* p. 392 (1985); and Evans et al. *J. Med. Chem.* 30:1229 (1987), which are incorporated herein by reference. Such compounds are often developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from the group consisting of: —CH$_2$NH—, —CH$_2$S—, —CH$_2$—CH$_2$—, —CH=CH— (cis and trans), —COCH$_2$—, —CH(OH)CH$_2$—, and —CH$_2$SO—, by methods well known in the art. Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo and Gierasch *Ann. Rev. Biochem.* 61:387 (1992), incorporated herein by reference); for example, by adding internal cysteine residues capable of forming intramolecular disulfide bridges which cyclize the peptide.

Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known (see Bowie et al. *Science* 253:164 (1991)). Those of skill in the art can recognize sequence motifs and structural conformations that may be used to define structural and functional domains in accordance with the invention.

The term "specific binding agent" refers to a natural or non-natural molecule that specifically binds to a target. Examples of specific binding agents include, but are not limited to, proteins, peptides, nucleic acids, carbohydrates, lipids, and small molecule compounds. In certain embodiments, a specific binding agent is an antibody. In certain embodiments, a specific binding agent is an antigen binding region of an antibody.

The term "EGFr-specific binding agent" refers to a specific binding agent that specifically binds any portion of an EGFr polypeptide. In certain embodiments, an EGFr-specific binding agent is an antibody that specifically binds an EGFr polypeptide. In certain embodiments, an EGFr-specific binding agent is a human antibody that specifically binds an EGFr polypeptide. In certain embodiments, an EGFr-specific binding agent is panitumumab. In certain embodiments, an EGFr-specific binding agent is an antigen binding region of an antibody specific for an EGFr polypeptide.

The term "specifically binds" refers to the ability of a specific binding agent to bind to a target with greater affinity than it binds to a non-target. In certain embodiments, specific binding refers to binding for a target with an affinity that is at least 10, 50, 100, 250, 500, or 1000 times greater than the affinity for a non-target. In certain embodiments, affinity is determined by an affinity ELISA assay. In certain embodiments, affinity is determined by a BIAcore assay. In certain embodiments, affinity is determined by a kinetic method. In certain embodiments, affinity is determined by an equilibrium/solution method. In certain embodiments, an antibody is said to specifically bind an antigen when the dissociation constant between the antibody and one or more of its recognized epitopes is $\leq 1$ μM, preferably $\leq 100$ nM and most preferably $\leq 10$ nM.

"Native antibodies and immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light chain variable domain is aligned with the variable domain of the heavy chain. Particular amino acid residues are believed to form an interface between the light- and heavy-chain variable domains (Chothia et al *J. Mol. Biol.* 186:651 (1985; Novotny and Haber, *Proc. Natl. Acad. Sci. U.S.A.* 82:4592 (1985); Chothia et al., *Nature* 342:877-883 (1989)).

The term "antibody" refers to both an intact antibody and to an antigen binding fragment thereof which competes with the intact antibody for specific binding. "Antigen binding fragment thereof" refers to a portion or fragment of an intact antibody molecule, wherein the fragment retains the antigen-binding function. Binding fragments are produced by recombinant DNA techniques, or by enzymatic or chemical cleavage of intact antibodies such as by cleavage with papain. Binding fragments include Fab, Fab', F(ab')$_2$, Fv, single-chain antibodies ("scFv"), Fd' and Fd fragments. Methods for producing the various fragments from monoclonal antibodies are well known to those skilled in the art (see, e.g., Pluckthun, 1992, Immunol. Rev. 130:151-188). An antibody other than a "bispecific" or "bifunctional" antibody is understood to have each of its binding sites be identical. An antibody substantially inhibits adhesion of a receptor to a counterreceptor when an excess of antibody reduces the quantity of receptor bound to counterreceptor by at least about 20%, 40%, 60%, or 80%, and more usually greater than about 85%, 90%, 95%, 96%, 97%, 98%, or 99% (as measured in an in vitro competitive binding assay).

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and terminal or internal amino acid sequencing by use of a spinning cup sequenator, or (2) to homogeneity by SDS-PAGE under reducing or non-reducing conditions using Coomassie blue or, preferably, silver stain. An isolated antibody includes the antibody in situ within recombinant cells since at least one component of the antibody's natural environment will not be present. Ordinarily, however, isolated antibody will be prepared by at least one purification step.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and heavy-chain variable domains. The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen-binding site of antibodies (see Kabat et al. (1991)). The constant domains are not involved directly in binding an antibody to an antigen, but exhibit various effector functions, such as participation of the antibody in antibody-dependent cellular toxicity.

"Fv" is the minimum antibody fragment which contains a complete antigen-recognition and binding site. In a two-chain Fv species, this region consists of a dimer of one heavy- and one light-chain variable domain in tight, non-covalent association. In a single-chain Fv species, one heavy- and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the VH-VL dimer. Collectively, the six CDRs confer antigen-binding specificity on the antibody. However, even a single variable domain (or half of an Fv comprising only three CDRs specific for an antigen) has the ability to recognize and bind antigen, although at a lower affinity than the entire binding site.

The term "hypervariable region" when used herein refers to the amino acid residues of an antibody which are responsible for antigen-binding. The hypervariable region generally comprises amino acid residues from a "complementarity determining region" or "CDR" (e.g. residues 24-34 (L1), 50-62 (L2), and 89-97 (L3) in the light chain variable domain and 31-55 (H1), 50-65 (H2) and 95-102 (H3) in the heavy chain variable domain; Kabat et al., *Sequences of Proteins of Immunological Interest,* 5$^{th}$ Ed. Public Health Service, National Institutes of Health, Bethesda, Md. (1991)) and/or those residues from a "hypervariable loop" (e.g. residues 26-32 (L1), 50-52 (L2) and 91-96 (L3) in the light chain variable domain and 26-32 ((H1), 53-55 (H2) and 96-1 01 (H3) in the heavy chain variable domain; Chothia and Lesk *J. Mol. Biol* 196:901-917 (1987)). "Framework Region" or "FR" residues are those variable domain residues other than the hypervariable region residues as herein defined.

The term "complementarity determining regions" or "CDRs," when used herein, refers to parts of immunological receptors that make contact with a specific ligand and determine its specificity. The CDRs of immunological receptors are the most variable part of the receptor protein, giving receptors their diversity, and are carried on six loops at the distal end of the receptor's variable domains, three loops coming from each of the two variable domains of the receptor.

"Antibody-dependent cell-mediated cytotoxicity" and "ADCC" refer to a cell-mediated reaction in which non-specific cytotoxic cells that express Fc receptors (FcRs) (e.g. Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. Fc expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362, or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et aL *PNAS* (*USA*) 95:652-656 (1988).

The term "epitope" includes any protein determinant capable of specific binding to an immunoglobulin and/or T-cell receptor. Epitopic determinants usually consist of chemically active surface groupings of molecules such as amino acids or sugar side chains and usually have specific three dimensional structural characteristics, as well as specific charge characteristics.

The term "agent" is used herein to denote a chemical compound, a mixture of chemical compounds, a biological macromolecule, or an extract made from biological materials.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In certain situations, the label or marker can also be therapeutic. Various methods of labeling polypeptides and glycoproteins are known in the art and may be used. Examples of labels for polypeptides include, but are not limited to, the following: radioisotopes or radionuclides (e.g., $^3$H,$^{14}$C,$^{15}$N,$^{35}$S, $^{90}$Y $^{99}$Tc, $^{111}$In, $^{125}$I, $^{131}$I), fluorescent labels (e.g., FITC, rhodamine, lanthanide phosphors), enzymatic labels (e.g., horseradish peroxidase, β-galactosidase, luciferase, alkaline phosphatase), chemiluminescent groups, biotinyl groups, and predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

The term "pharmaceutical agent or drug" as used herein refers to a chemical compound or composition capable of inducing a desired therapeutic effect when properly administered to a patient. Other chemistry terms herein are used according to conventional usage in the art, as exemplified by *The McGraw-Hill Dictionary of Chemical Terms* (Parker, S., Ed., McGraw-Hill, San Francisco (1985)), incorporated herein by reference.

The term "anti-cancer agent" is used herein to refer to agents that have the functional property of inhibiting a development or progression of a neoplasm in a human, particularly a malignant (cancerous) lesion, such as a carcinoma, sarcoma, lymphoma, or leukemia. Inhibition of metastasis is frequently a property of anti-cancer agents.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, 90%, 95%, 96%, 97%, 98%, or 99%. Most preferably, the object species is purified to essential homogeneity (contaminant species cannot be detected in the composition by conventional detection methods) wherein the composition consists essentially of a single macromolecular species.

The terms "patient" and "subject" include human and animal subjects.

The terms "mammal" and "animal" for purposes of treatment refer to any animal classified as a mammal, including humans, domestic and farm animals, and zoo, sports, or pet animals, such as dogs, horses, cats, cows, etc. Preferably, the mammal is human.

The term "disease state" refers to a physiological state of a cell or of a whole mammal in which an interruption, cessation, or disorder of cellular or body functions, systems, or organs has occurred.

The terms "treat" or "treatment" refer to. both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

A statement that a treatment is "efficacious" means that the treatment is useful for treating the disease or condition for which the treatment is administered.

A "disorder" is any condition that would benefit from one or more treatments. This includes chronic and acute disorders or disease including those pathological conditions which predispose the mammal to the disorder in question. Non-limiting examples of disorders to be treated herein include benign and malignant tumors, leukemias, and lymphoid malignancies, in particular breast, rectal, ovarian, stomach, endometrial, salivary gland, lung, kidney, colon, thyroid, pancreatic, prostate or bladder cancer. A preferred disorder to be treated in accordance with the present invention is a malignant tumor, such as colorectal cancer, cervical cancer (e.g., cervical intraepithelial squamous and glandular neoplasia), lung cancer, renal cell carcinoma (RCC), esbphageal tumors, epithelial malignant tumors, and carcinoma-derived cell lines.

A "disease or condition related to an EGFr polypeptide" includes at least one disease or condition selected from: a disease or condition caused by an EGFr polypeptide; a disease or condition exacerbated by an EGFr polypeptide; a disease or condition contributed to by an EGFr polypeptide; and a disease or condition that is associated with the presence of an EGFr polypeptide. In certain embodiments, the disease or condition related to an EGFr polypeptide may exist in the absence of the EGFr polypeptide. In certain embodiments, an increase or decrease in the amount of EGFr polypeptide causes a disease or condition related to an EGFr polypeptide. In certain embodiments, a disease or condition related to an EGFr polypeptide may be exacerbated by an increase or decrease in the amount of EGFr polypeptide. In certain embodiments, a disease or condition related to an EGFr polypeptide is a cancer. An "EGFr-related cancer" includes at least one cancer selected from: a cancer which is caused by an EGFr polypeptide, a cancer which is exacerbated by an EGFr polypeptide, a cancer which is contributed to by an EGFr polypeptide, and a cancer which is associated with an EGFr polypeptide. Exemplary EGFr-related cancers include, but are not limited to, colorectal cancer, lung cancer (including, but not limited to, non small cell lung carcinoma), breast cancer, kidney cancer, colon cancer, gastric cancer, brain cancer, bladder cancer, head and neck cancers, ovarian cancer, and prostate cancer.

In "combined therapy" or "combination therapy," patients are treated with an EGFr-specific binding agent in combination with a chemotherapeutic or anti-cancer agent and/or radiation therapy. In certain embodiments, an EGFr-related cancer is treated under protocol by the addition of a specific binding agent to an EGFr polypeptide to standard first and second line therapy. In certain embodiments, protocol designs will address effectiveness as assessed by reduction in tumor mass as well as the ability to reduce usual doses of standard chemotherapy. In certain embodiments, these dosage reductions will allow additional and/or prolonged therapy by reducing dose-related toxicity of the chemotherapeutic agent.

"Monotherapy" refers to the treatment of a disorder by administering an EGFr-specific binding agent to patients without an accompanying chemotherapeutic or anti-cancer agent or radiation therapy.

Certain Exemplary Embodiments

Certain Exemplary Methods of Determining EGFr Gene Copy Number

In various embodiments, the EGFr gene copy number of a sample can be determined in a variety of ways known in the art. Exemplary methods include, but are not limited to, hybridization-based assays, amplification-based assays, and by detection of gene transcription and protein expression.

In certain embodiments, a hybridization-based assay is used to determine the EGFr gene copy number in a sample. In certain embodiments, the hybridization-based assay is fluorescent in situ hybridization ("FISH") (see, e.g., Angerer, Meth. Enzymol. 152: 649 (1987); Pinkel et al., Proc. Natl. Acad. Sci. U.S.A. 85:9138-42 (1988)). In certain such embodiments, the sample is fixed. In certain such embodiments, the sample is treated to increase the accessibility of one or more target nucleic acids. In certain such embodiments, the sample is exposed to one or more probes that specifically bind to the EGFr gene. In certain embodiments, one or more probes that specifically bind to the EGFr gene are labeled. In certain embodiments, the sample is also exposed to one or more probes that specifically bind to at least one reference nucleotide sequence. In certain embodiments, one or more probes that specifically bind to at least one reference nucleotide sequence are labeled. In certain embodiments, one or more probes that specifically bind to the EGFr gene are labeled with a different label than the label of one or more probes that specifically bind to at least one reference nucleotide sequence. In certain embodiments, at least one reference nucleotide sequence is located on chromosome 7. In certain embodiments, two copies of at least one reference nucleotide sequence are present in each cell in the sample. In certain embodiments, at least one reference nucleotide sequence is a centromeric sequence. In certain embodiments, labeled probes are detected by fluorescent microscopy. In certain embodiments, the EGFr gene copy number is compared to the copy number of at least one reference nucleotide sequence. In certain embodiments, an increased copy number of the EGFr gene in the test sample relative to the copy number of the at least one reference nucleotide sequence predicts that an EGFr-specific binding agent treatment will be efficacious in treating an EGFr-related cancer in the subject.

In certain embodiments, the number of nuclei present in a sample is determined. In certain embodiments, the number of nuclei present in a sample is determined by fluorescence microscopy. In certain embodiments, the EGFr gene copy number is compared to the number of nuclei in the sample. In certain embodiments, the ratio of the EGFr gene copy number to the number of nuclei is expected to be 2 in a normal sample. In certain embodiments, a ratio of EGFr gene copy number to number of nuclei greater than two predicts that an EGFr-specific binding agent treatment will be efficacious in treating an EGFr-related cancer in the subject.

In certain embodiments, a hybridization-based assay is a Southern blot (see, e.g., Sambrook and Russell, "Southern Hybridization" in Molecular Cloning: A Laboratory Manual, 3d ed., Cold Spring Harbor Lab. Press: Cold Spring Harbor (2001)). In certain such embodiments, nucleic acids from the sample are separated by electrophoresis. In certain embodiments, the separated nucleic acids are transferred to a solid support. Exemplary solid supports include, but are not limited to, nitrocellulose; nylon; glass; quartz; diazotized membranes, including, but not limited to, paper or nylon; silicones; polyformaldehyde; cellulose; cellulose acetate; plastics including, but not limited to, polyethylene, polypropylene, and polystyrene; paper; ceramics; metals; metalloids; semiconductive materials; and substances that form gels, including, but not limited to, gelatins, lipopolysaccharides, silicates, agarose, and polyacrylamides. In certain such embodiments, the separated nucleic acids on the solid support are exposed to one or more probes that specifically bind to the EGFr gene. In certain embodiments, one or more probes that specifically bind to the EGFr gene are labeled. In certain embodiments, separated nucleic acids on the solid support are also exposed to one or more probes that specifically bind to at least one reference nucleotide sequence. In certain embodiments, one or. more probes that specifically bind to at least one reference nucleotide sequence are labeled. In certain embodiments, one or more probes that specifically bind to the EGFr gene are labeled with a different label than the label of one or more probes that specifically bind to at least one reference nucleotide sequence. In certain embodiments, at least one reference nucleotide sequence is located on chromosome 7. In certain embodiments, two copies of at least one reference nucleotide sequence are present in each cell in the sample. In certain embodiments, at least one reference nucleotide sequence is a centromeric sequence. In certain embodiments, labeled probes are detected. In certain embodiments, the EGFr gene copy number is compared to the copy number of at least one reference nucleotide sequence. In certain embodiments, an increased copy number of the EGFr gene in the test sample relative to the copy number of the at least one reference nucleotide sequence predicts that an EGFr-specific binding agent treatment will be efficacious in treating an EGFr-related cancer in the subject.

In certain embodiments, the hybridization-based assay is a sandwich assay (see, e.g., Hames and Higgins, Nucleic Acid Hybridization, A Practical Approach, IRL Press (1985); Gall et al., Proc. Natl. Acad. Sci. U.S.A. 63: 378-383 (1969); and John et al., Nature 223: 582-587 (1969)). In certain embodiments, a nucleic acid that specifically binds to the EGFr gene is immobilized to a solid support. Exemplary solid supports include, but are not limited to, nitrocellulose; nylon; glass; quartz; diazotized membranes, including, but not limited to, paper or nylon; silicones; polyformaldehyde; cellulose; cellulose acetate; plastics including, but not limited to, polyethylene, polypropylene, and polystyrene; paper; ceramics; metals; metalloids; semiconductive materials; and substances that form gels, including, but not limited to, gelatins, lipopolysaccharides, silicates, agarose, and polyacrylamides. Exemplary types of immobilization include, but are not limited to, covalent bonding or linking via one or more functional groups, including, but not limited to, carboxylic acids, aldehydes, amino groups, cyano groups, ethylenic groups, hydroxyl groups, and mercapto groups.

In certain embodiments, an immobilized nucleic acid that specifically binds to the EGFr gene is exposed to nucleic acids from a sample. In certain embodiments, one or more EGFr genes hybridize to the immobilized nucleic acid that specifically binds to the EGFr gene. In certain embodiments, a wash step removes unhybridized and/or mishybridized sample nucleic acids from the immobilized nucleic acid. In certain embodiments, the EGFr gene:immobilized nucleic acid complex is exposed to an EGFr gene-specific probe. In certain embodiments, the probe is labeled. In certain embodiments, the label is detected quantitatively. In certain embodiments, the EGFr gene copy number in a sample is compared to the copy number of at least one reference sequence in that sample. In certain embodiments, the EGFr gene. copy number in a tumorigenic sample is compared to the EGFr gene copy number in a normal sample. In certain embodiments, the EGFr gene copy number in a malignant sample is compared to the EGFr gene copy number in a normal sample.

In certain embodiments, the EGFr gene copy number of a sample is determined by an amplification-based assay. Exemplary amplification-based assays include, but are not limited to, quantitative PCR (see, e.g., Poropat et al., Clinical Chem. 44:724-730,1998), ligase chain reaction (see, e.g., Wu et al., Genomics 4: 560 (1989); Landegren et al., Science 241: 1077 (1988); and Barringer et al., Gene 89: 117 (1990)), transcription amplification (see, e.g., Kwoh et al., Proc. Natl. Acad. Sci. U.S.A. 86: 1173 (1989)); competitive PCR (see, e.g., Honda et al., J. Exp. Botany 53: 1515-20 (2002)); and self-sustained sequence replication (see, e.g., Guatelli et al., Proc. Nat. Acad. Sci. U.S.A. 87: 1874 (1990)).

In certain embodiments, the EGFr gene copy number of a sample is determined by quantitating the amount of EGFr gene transcript in the sample, using any of the methods described above.

In certain embodiments, the EGFr gene copy number of a sample is determined by quantitation of EGFr polypeptide expression, using methods known in the art. Exemplary polypeptide quantitation methods include, but are not limited to, light absorption analysis, including, but not limited to, measuring the absorbance at 280 nm; incubation of sample extracts with labeled anti-EGFr antibodies followed by quantitation of the specifically bound anti-EGFr antibodies; and chromatography, including, but not limited to, electrophoresis followed by densitometry or Western analysis, and column chromatography coupled to a detection device.

In certain embodiments, an array-based system is used to determine the EGFr copy number of a sample. Exemplary array-based systems include, but are not limited to, array-based systems involving hybridization-based assays, amplification-based assays, quantitation of gene transcription, and quantitation of protein expression. Certain exemplary array. methodologies are described below.

Certain Exemplary Arrays

In certain embodiments, the EGFr gene copy number in a sample from one or more subjects is determined using microarray technology, as is known in the art (see, e.g., Pollack et al., Nature Genetics 23: 41-46 (1999); Pastinen, Genome Res. 7: 606-614 (1997); Jackson, Nature Biotechnology 14: 1685 (1996); Chee, Science 274: 610 (1995); and Pinkel et al., Nature Genetics 20:207-211 (1998)). In certain embodiments, the EGFr gene copy number in two or more samples from one or more subjects is determined using microarray technology. In certain such embodiments, two or more samples are taken from a single subject. In certain such embodiments, one of the two or more samples is from an EGFr-related tumor and another of the two or more samples is from nontumorigenic normal tissue.

In certain embodiments, a sample is not treated prior to determination of the EGFr gene copy number. In certain embodiments, a sample is treated prior to the determination.of the EGFr gene copy number. In certain embodiments, the EGFr gene copy number in a sample is determined both prior to and after treatment of the sample.

In certain embodiments, microarrays comprising one or more molecules that specifically bind to an EGFr gene are provided. In certain embodiments, microarrays comprising one or more nucleic acids complementary to an EGFr gene are provided. In certain such embodiments, nucleic acids are extracted from one or more samples from one or more subjects and the extracted nucleic acids are exposed to one or more nucleic acids complementary to an EGFr gene in the microarray to form an EGFr gene hybridization complex. In certain such embodiments, the amount of EGFr gene hybridization complex in a microarray is quantitated. In certain such embodiments, the quantitation is by binding of a labeled molecule to an EGFr gene hybridization complex and quantitatively detecting the label. In certain such embodiments, the EGFr gene is labeled and quantitatively detected after formation of the EGFr gene hybridization complex.

In certain embodiments, a candidate treatment for an EGFr-related cancer is screened using microarray technology. In certain such embodiments, the EGFr gene copy number is determined in a first sample obtained from a patient prior to the administration of the treatment to the patient, and the EGFr gene copy number is determined in a second sample obtained from the patient at a time following the administration of the treatment. In certain such embodiments, the EGFr gene copy numbers of the first sample and of the second sample are compared, wherein a decrease in the EGFr gene copy number in the second sample relative to the EGFr gene copy number of the first sample indicates that the treatment is effective in the patient.

In certain embodiments, the presence or absence of one or more EGFr polypeptides in one or more samples is assessed using microarray technology. In certain such embodiments, mRNA is first extracted from a cell or tissue sample and is subsequently converted to cDNA, which is hybridized to the microarray. In certain such embodiments, the presence or absence of cDNA that is specifically bound to the microarray is indicative of the presence or absence of the EGFr polypeptide. In certain such embodiments, the expression level of the one or more EGFr polypeptides is assessed by quantitating the amount of cDNA that is specifically bound to the microarray. In certain such embodiments, the cell or tissue is treated prior to the assessment, and the ability of the treatment to affect expression of the one or more EGFr polypeptides is also assessed.

In certain embodiments, microarrays comprising one or more EGFr polypeptides are provided (see, e.g., McBeath et al., Science, 289:1760-1763, 2000). In certain embodiments, candidate specific binding agents to one or more EGFr polypeptides are screened using an EGFr polypeptide microarray. In certain embodiments, microarrays comprising one or more specific binding agents to an EGFr polypeptide are provided. In certain embodiments, the quantity of an EGFr polypeptide in one or more samples is assessed.

Certain Exemplary Specific Binding Agents and Antibodies

In certain embodiments, an EGFr-specific binding agent is provided. In certain such embodiments, the EGFr-specific binding agent is an antibody or an antigen-binding fragment thereof.

In certain embodiments, monoclonal antibodies may be made using the hybridoma method first described by Kohler et al., *Nature* 256: 495 (1975). In certain embodiments, monoclonal antibodies may be made by recombinant DNA methods (U.S. Pat. No. 4,816,567).

In certain embodiments of the hybridoma method, a mouse or other appropriate host animal, including, but not limited to, a hamster or macaque monkey, is immunized to elicit lymphocytes that produce or are capable of producing antibodies that will specifically bind to the protein used for immunization. In certain embodiments, lymphocytes may be immunized in vitro. In certain embodiments, lymphocytes or lymphocytes enriched for B cells are fused with myeloma cells by an electrocell fusion process or by using a suitable fusing agent, such as polyethylene glycol, to form a hybridoma cell (Goding, *Monoclonal Antibodies: Principles and Practice*, pp. 59-103, [Academic Press, 1996]).

In certain embodiments, hybridoma cells are seeded and grown in a suitable culture medium that preferably contains one or more substances that inhibit the growth or survival of the unfused, parental myeloma cells. In certain embodiments, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

In certain embodiments, myeloma cells are selected that fuse efficiently, support stable high-level production of antibody by the selected antibody-producing cells, and are sensitive to a medium such as HAT medium. Exemplary myeloma cell lines include, but are not limited to, murine myeloma lines, such as those derived from MOP-21 and MC.-11 mouse tumors available from the Salk Institute Cell Distribution Center, San Diego, Calif. USA, and SP-2 or X63-Ag8-653 cells available from the American Type Culture Collection, Rockville, Md. USA. In certain embodiments, human myeloma and/or mouse-human heteromyeloma cell lines are used for the production of human monoclonal antibodies (Kozbor, *J. Immunol.* 133: 3001 (1984); Brodeur et al., *Monoclonal Antibody Production Techniques and Applications*, pp. 51-63, Marcel Dekker, Inc., New York, [1987]).

In certain embodiments, culture medium in which hybridoma cells are growing is assayed for production of monoclonal antibodies directed against the antigen. In certain embodiments, the binding specificity of monoclonal antibodies produced by hybridoma cells is determined by immunoprecipitation or by an in vitro binding assay. Exemplary binding assays include, but are not limited to, a radioimmunoassay (RIA), an enzyme-linked immunosorbent assay (ELISA), and the Scatchard analysis of Munson et al., *Anal. Biochem.* 107: 220 (1980).

In certain embodiments, after hybridoma cells are identified that produce antibodies of the desired specificity, affinity, and/or activity, the cells may be subcloned by limiting dilution procedures and grown by standard methods (Goding, *Monoclonal Antibodies: Principles and Practice*, pp. 59-103, Academic Press, 1996). Exemplary culture media for this purpose include, but are not limited to, DMEM and RPMI-1640 medium. In certain embodiments, hybridoma cells may be grown in vivo as ascites tumors in an animal.

In certain embodiments, monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

In certain embodiments, a nucleic acid encoding the monoclonal antibodies is readily isolated and sequenced using conventional procedures (e.g., by using oligonucleotide probes that are capable of binding specifically to genes encoding the heavy and light chains of the monoclonal antibodies). In certain such embodiments, the hybridoma cells serve as a preferred source of such nucleic acid. In certain embodiments, isolated polynucleotide may be placed into expression vectors. In certain such embodiments, the expression vectors are transfected into host cells to obtain the synthesis of monoclonal antibodies in the recombinant host cells. Exemplary host cells include, but are not limited to, *E. coli* cells, simian COS cells, Chinese hamster ovary (CHO) cells, or myeloma cells that do not otherwise produce immunoglobulin protein. In certain embodiments, the nucleic acid may be modified, for example, by covalently joining to the immunoglobulin coding sequence all or part of the coding sequence for a non-immunoglobulin polypeptide, creating a "chimeric" or "hybrid" antibody.

In certain embodiments, non-immunoglobulin polypeptides are substituted for the constant domains of an antibody. In certain embodiments, non-immunoglobulin polypeptides are substituted for the variable domains of one antigen-combining sites of an antibody to create a chimeric bivalent antibody comprising one antigen-combining site having specificity for a target antigen and another antigen-combining site having specificity for a different antigen.

In certain embodiments, chimeric or hybrid antibodies can be prepared in vitro using known methods in synthetic protein chemistry, including, but not limited to, those involving crosslinking agents. In certain such embodiments, immunotoxins can be constructed using a disulfide exchange reaction or by forming a thioether bond. Exemplary reagents for this purpose include, but are not limited to, iminothiolate and methyl-4-mercaptobutyrimidate.

In certain embodiments, human antibodies to a target antigen are provided. In certain embodiments, hybridoma technology is extended to create human antibodies using heteromyelomas (mouse x human hybrid myelomas) as fusion partners (see, e.g., Kozbor, *J. Immunol.* 133: 3001 (1984); Brodeur, et al., *Monoclonal Antibody Production Techniques and Applications*, pp. 51-63, Marcel Dekker, Inc., New York, 1987). In certain embodiments, human antibody-secreting cells can be immortalized by infection with the Epstein-Barr virus (EBV) (James and Bell, *J. Immunol. Methods* 100: 5-40 [1987]). In certain embodiments, the immortalization of human B cells can be achieved by introducing a defined combination of transforming genes (Hahn et al., *Nature* 400: 464-468 [1999]).

In certain embodiments, transgenic animals (e.g. mice) that are capable, upon immunization, of producing a repertoire of human antibodies in the absence of endogenous immunoglobulin production are used to make human antibodies (see, e.g., Jakobovits et al., *Nature* 362: 255-258 [1993]; Lonberg and Huszar, *Int. Rev. Immunol.* 13: 65-93 [1995]; Fishwild et al., *Nat. Biotechnol.* 14: 845-851 [1996]; Mendez et al., *Nat. Genet.* 15: 146-156 [1997]; Green, *J. Immunol. Methods* 231: 11-23 [1999]; Tomizuka et al., *Proc. Natl. Acad. Sci. USA* 97: 722-727 [2000]; reviewed in Little et al., *Immunol. Today* 21: 364-370 [2000]). It has been described that the homozygous deletion of the antibody heavy chain joining region ($J_H$) gene in chimeric and germ line mutant mice results in complete inhibition of endogenous antibody production (Jakobovits et al., *Proc. Natl. Acad. Sci. USA* 90: 2551-2555 [1993]). Transfer of the human germ-line immunoglobulin gene array in such germ line mutant mice results in the production of human antibodies upon antigen challenge (Jakobovits et al., *Nature* 362: 255-258 [1993]).

Mendez et al. (*Nature Genetics* 15: 146-156 [1997]) have generated a line of transgenic mice designated "Xenomouse®II" that, when challenged with an antigen, generates high affinity fully human antibodies. This was achieved by germ-line integration of megabase human heavy chain and light chain loci into mice with deletion into endogenous JH segment. The XenoMouse® II harbors 1,020 kb of human heavy chain locus containing approximately 66 $V_H$ genes, complete $D_H$ and $J_H$ regions and three different constant regions (μ, δ and γ), and also harbors 800 kb of human κ locus containing 32 Vκ genes, Jκ segments and Cκ genes. In certain embodiments, the antibodies produced in those mice closely resemble those seen in humans in all respects, including gene rearrangement, assembly, and repertoire. In certain embodiments, the human antibodies are preferentially expressed over endogenous antibodies due to a deletion in the endogenous $J_H$ segment that prevents gene rearrangement in the murine locus.

In certain embodiments, a transgenic animal comprising human immunoglobulin genes (e.g., the Xenomouse® II (Abgenix, Inc.)) may be immunized with an antigen of particular interest, such as an EGFr polypeptide. In certain embodiments, sera from those immunized animals is screened for antibody reactivity against the initial antigen. In certain embodiments, lymphocytes are isolated from lymph nodes or spleen cells and may further be enriched for B cells by selecting for CD138-negative and CD19+cells. In certain embodiments, those B cell cultures (BCCs) are fused to myeloma cells to generate hybridomas as detailed above. In certain embodiments, those B cell cultures are screened further for reactivity against the initial antigen. Such screening includes, but is not limited to, ELISA, a competition assay with known antibodies that bind the antigen of interest, and in vitro binding to transiently transfected CHO cells expressing the antigen. In certain embodiments, single B cells secreting antibodies of interest are identified by a specific hemolytic plaque assay. In certain such embodiments, cells targeted for lysis are sheep red blood cells (SRBCs) coated with the antigen. In certain such embodiments, the formation of a plaque indicates specific antigen-mediated lysis of the target cells, and thus the presence of a B cell culture secreting the immunoglobulin of interest and complement. In certain such embodiments, the single antigen-specific plasma cell in the center of the plaque can be isolated and used for isolation of mRNA.

In certain embodiments, the nucleic acid encoding the variable region of the antibody secreted can be cloned using reverse-transcriptase PCR. In certain embodiments, the cloned nucleic acid is further inserted into a suitable expression vector, such as a vector cassette such as a pcDNA, or a pcDNA vector containing the constant domains of immunoglobulin heavy and light chain. In certain embodiments, the generated vector is transfected into host cells, (i.e., CHO cells), and cultured in conventional nutrient media modified as appropriate for inducing promoters, selecting transformants, or amplifying the genes encoding the desired sequences.

In certain embodiments, phage display technology is used to produce human antibodies and antibody fragments in vitro, from immunoglobulin variable (V) domain gene repertoires from unimmunized donors (see, e.g., McCafferty et al., *Nature* 348: 552-553 [1990]; reviewed in Kipriyanov and Little, *Mol. Biotechnol.* 12: 173-201 [1999]; Hoogenboom and Chames, *Immunol. Today*21: 371-378 [2000]). In certain such embodiments, antibody V domain genes are cloned in-frame into either a major or minor coat protein gene of a filamentous bacteriophage, such as M13 or fd, and displayed as functional antibody fragments on the surface of the phage particle. In certain embodiments, the filamentous particle contains a single-stranded DNA copy of the phage genome, and selections based on the functional properties of the antibody also result in selection of the gene encoding the antibody exhibiting those properties. Phage display can be performed in a variety of formats, including, but not limited to, those identified in the following documents: Johnson and Chiswell, *Current Opinion in Structural Biology* 3: 564-571 [(1993)]; Winter et al., *Annu. Rev. Immunol.* 12: 433-455 [1994]; Dall'Acqua and Carter, *Curr. Opin. Struct Biol.* 8: 443-450 [1998]; and Hoogenboom and Chames, *Immunol. Today*21: 371-378 [2000]. Sources of V-gene segments for phage display include, but are not limited to, a small random combinatorial library of V genes derived from the spleens of immunized mice (Clackson et al., (*Nature* 352: 624-628 [1991]) and a repertoire of V genes from unimmunized human donors (Marks et al., *J. Mol. Biol.* 222: 581-597 (1991), or Griffiths et al., *EMBO J.* 12: 725-734 (1993)).

In certain embodiments, in a natural immune response, antibody genes accumulate mutations at a high rate (somatic hypermutation). In certain embodiments, some of the changes introduced confer higher affinity. In certain embodiments, B cells displaying high-affinity surface immunoglobulin are preferentially replicated and differentiated during subsequent antigen challenge. In certain embodiments, that natural process can be mimicked by employing the technique known as "chain shuffling" (Marks et al., *Bio/Technol.* 10: 779-783 [1992]). In certain such embodiments, the affinity of "primary" human antibodies obtained by phage display can be improved by sequentially replacing the heavy and light chain V region genes with repertoires of naturally occurring variants (repertoires) of V domain genes obtained from unimmunized donors, allowing the production of antibodies and antibody fragments with affinities in the nM range. In certain embodiments, a very large phage antibody repertoire is constructed (also known as "the mother-of-all libraries"), as described by Waterhouse et al., *Nucl. Acids Res.* 21: 2265-

2266 (1993). In certain such embodiments, a high affinity human antibody is directly isolated from a large phage library (see, e.g., Griffiths et al., *EMBO J.* 13: 3245-3260 (1994)). In certain embodiments, gene shuffling can be used to derive human antibodies from rodent antibodies, where the human antibody has similar affinities and specificities to the starting rodent antibody. In certain such embodiments, the heavy or light chain V domain gene of rodent antibodies obtained by phage display technique is replaced with a repertoire of human V domain genes, creating rodent-human chimeras (also referred to as "epitope imprinting"). In certain embodiments, selection of variable regions by the antigen results in isolation of human variable regions capable of restoring a functional antigen-binding site, i.e. the epitope governs (imprints) the choice of partner. In certain embodiments, when the process is repeated in order to replace the remaining rodent V domain, a human antibody is obtained which has no framework or CDR residues of rodent origin (see, e.g., PCT patent application WO 93/06213).

Certain Exemplary Treatments

In certain embodiments, anti-EGFr-specific binding agents may have therapeutic use by inclusion in an EGFr specific binding agent treatment. In this application, when discussing the use of EGFr-specific binding agents to treat diseases or conditions, such use may include use of the EGFr-specific binding agents themselves; compositions comprising EGFr-specific binding agents; and/or combination therapies comprising EGFr-specific binding agents and one or more additional active ingredients. When EGFr-specific binding agents are used to "treat" a disease or condition, such treatment may or may not include prevention of the disease or condition. In certain embodiments, EGFr-specific binding agents can block the interaction of the EGF receptor with its ligand, EGF. In certain embodiments, EGFr-specific binding agents can activate the EGF receptor. In certain embodiments, EGFr-specific binding agents can constitutively activate the EGF receptor. In certain embodiments, EGFr-specific binding agents can block the activation of the EGF receptor. In certain embodiments, EGFr-specific binding agents can constitutively block the activation of the EGF receptor.

In certain embodiments, an EGFr-specific binding agent is administered alone. In certain embodiments, an EGFr-specific binding agent is administered prior to the administration of at least one other therapeutic agent. In certain embodiments, an EGFr-specific binding agent is administered concurrent with the administration of at least one other therapeutic agent. In certain embodiments, an EGFr-specific binding agent is administered subsequent to the administration of at least one other therapeutic agent. Exemplary therapeutic agents, include, but are not limited to, at least one other cancer therapy agent. Exemplary cancer therapy agents include, but are not limited to, radiation therapy and chemotherapy.

In certain embodiments, EGFr-specific binding agent pharmaceutical compositions can be administered in combination therapy, i.e., combined with other agents. In certain embodiments, the combination therapy comprises an EGFr-specific binding agent, in combination with at least one anti-angiogenic agent. Exemplary agents include, but are not limited to, in vitro synthetically prepared chemical compositions, antibodies, antigen binding regions, radionuclides, and combinations and conjugates thereof. In certain embodiments, an agent may act as an agonist, antagonist, allosteric modulator, or toxin. In certain embodiments, an agent may act to inhibit or stimulate its target (e.g., receptor or enzyme activation or inhibition), and thereby promote cell death or arrest cell growth.

Exemplary chemotherapy treatments include, but are not limited to, anti-cancer agents including, but not limited to, alkylating agents including, but not limited to: nitrogen mustards, including, but not limited to, mechlorethamine, cyclophosphamide, ifosfamide, melphalan and chlorambucil; nitrosoureas, including, but not limited to, carmustine BCNU, lomustine, CCNU, and semustine, methyl-CCNU; Temodal™, temozolamide; ethylenimines/methylmelamine, including, but not limited to, thriethylenemelamine (TEM), triethylene, thiophosphoramide, thiotepa, hexamethylmelamine (HMM), and altretamine; alkyl sulfonates, including, but not limited to, busulfan; triazines, including, but not limited to, dacarbazine (DTIC); antimetabolites, including, but not limited to, folic acid analogs such as methotrexate and trimetrexate; pyrimidine analogs, including, but not limited to, 5-fluorouracil (5FU), fluorodeoxyuridine, gemcitabine, cytosine arabinoside (AraC, cytarabine), 5-azacytidine, and 2,2'-difluorodeoxycytidine; purine analogs, including, but not limited to, 6-mercaptopurine, 6-thioguanine, azathioprine, 2'-deoxycoformycin (pentostatin), erythrohydroxynonyladenine (EHNA), fludarabine phosphate, cladribine, and 2-chlorodeoxyadenosine (2-CdA); natural products, including, but not limited to, antimitotic drugs such as paclitaxel; vinca alkaloids, including, but not limited to, vinblastine (VLB), vincristine, and vinorelbine; taxotere; estramustine and estramustine phosphate; ppipodophylotoxins, including, but not limited to, etoposide and teniposide; antibiotics, including, but not limited to, actinomycin D, daunomycin, rubidomycin, doxorubicin, mitoxantrone, idarubicin, bleomycins, plicamycin, mithramycin, mitomycin C, and actinomycin; enzymes, including, but not limited to, L-asparaginase; biological response modifiers, including, but not limited to, interferon-alpha, IL-2, G-CSF, and GM-CSF; doxycyckine; irinotecan hydrochloride; miscellaneous agents, including, but not limited to, platinum coordination complexes such as cisplatin and carboplatin; anthracenediones, including, but not limited to, mitoxantrone; substituted urea, including, but not limited to, hydroxyurea; methylhydrazine derivatives, including, but not limited to, N-methylhydrazine (MIH) and procarbazine; adrenocortical suppressants, including, but not limited to, mitotane (o,p'-DDD) and aminoglutethimide; hormones and antagonists, including, but not limited to, adrenocorticosteroid antagonists such as prednisone and equivalents, dexamethasone and aminoglutethimide; Gemzar™, gemcitabine; progestin, including, but not limited to, hydroxyprogesterone caproate, medroxyprogesterone acetate and megestrol acetate; estrogen, including, but not limited to, diethylstilbestrol and ethinyl estradiol equivalents; antiestrogen, including, but not limited to, tamoxifen; androgens, including, but not limited to, testosterone propionate and fluoxymesterone/equivalents; antiandrogens, including, but not limited to, flutamide, gonadotropin-releasing hormone analogs and leuprolide; oxaliplatin, Eloxatin®, capecitabine, Xeloda®, pemetrexed, Alimta®, letrozole, Femara®, anastrozole, Arimidex®, and non-steroidal antiandrogens, including, but not limited to, flutamide.

Exemplary cancer therapies, which may be administered with an EGFr-specific binding agent, include, but are not limited to, targeted therapies. Examples of targeted therapies include, but are not limited to, use of therapeutic antibodies. Exemplary therapeutic antibodies, include, but are not limited to, mouse, mouse-human chimeric, CDR-grafted, humanized, and human antibodies, and synthetic antibodies, including, but not limited to, those selected by screening antibody libraries. Exemplary antibodies include, but are not limited to, those which bind to cell surface proteins Her2, CDC20, CDC33, and mucin-like glycoprotein, and optionally induce a cytostatic and/or cytotoxic effect on tumor cells displaying these proteins. Exemplary antibodies also include, but are not limited to, HERCEPTIN™, trastuzumab, which may be used to treat breast cancer and other forms of cancer; RITUXAN™, rituximab, ZEVALIN™, ibritumomab tiuxetan, and LYMPHOCIDE™, epratuzumab, which may be used to treat non-Hodgkin's lymphoma and other forms of cancer; GLEEVEC™, imatinib mesylate, which may be used to treat chronic myeloid leukemia and gastrointestinal stromal tumors; and BEXXAR™, iodine 131 tositumomab, which may be used for treatment of non-Hodgkin's lymphoma. Certain exemplary antibodies also include ERBITUX™; IMC-C225; Iressa™; gefitinib; TARCEVA™, ertinolib; KDR (kinase domain receptor) inhibitors; anti VEGF antibodies and antagonists (e.g., Avastin™ and VEGAF-TRAP); anti VEGF receptor antibodies and antigen binding regions; anti-Ang-1 and Ang-2 antibodies and antigen binding regions; antibodies to Tie-2 and other Ang-1 and Ang-2 receptors; Tie-2 ligands; antibodies against Tie-2 kinase inhibitors; and Campath®, alemtuzumab. In certain embodiments, cancer therapy agents are other polypeptides which selectively induce apoptosis in tumor cells, including, but not limited to, TNF-related polypeptides such as TRAIL.

In certain embodiments, cancer therapy agents are anti-angiogenic agents which decrease angiogenesis. Certain such agents include, but are not limited to, ERBITUX™, IMC-C225; KDR (kinase domain receptor) inhibitory agents (e.g., antibodies and antigen binding regions that specifically bind to the kinase domain receptor); anti-VEGF agents (e.g., antibodies or antigen binding regions that specifically bind VEGF, or soluble VEGF receptors or a ligand binding region thereof) such as AVASTIN™ or VEGF-TRAP™; anti-VEGF receptor agents (e.g., antibodies or antigen binding regions that specifically bind thereto); EGFR inhibitory agents such as IRESSA™, gefitinib, TARCEVA™, erlotinib, anti-Ang1 and anti-Ang2 agents (e.g., antibodies or antigen binding regions specifically binding thereto or to their receptors, e.g., Tie2/Tek); and anti-Tie-2 kinase inhibitory agents (e.g., antibodies or antigen binding regions that specifically bind thereto). In certain embodiments, the pharmaceutical compositions may also include one or more agents (e.g., antibodies, antigen binding regions, or soluble receptors) that specifically bind and inhibit the activity of growth factors, such as antagonists of hepatocyte growth factor (HGF, also known as Scatter Factor), and antibodies or antigen binding regions that specifically bind its receptor "c-met."

Exemplary anti-angiogenic agents include, but are not limited to, Campath, IL-8, B-FGF, Tek antagonists (Ceretti et al., U.S. Patent Application Publication No. 2003/0162712; U.S. Pat. No. 6,413,932); anti-TWEAK agents (e.g., specifically binding antibodies or antigen binding regions, or soluble TWEAK receptor antagonists; see, e.g., Wiley, U.S. Pat. No. 6,727,225); ADAM disintegrin domain to antagonize the binding of integrin to its ligands (Fanslow et al., U.S. Patent Application Publication No. 2002/0042368); specifically binding anti-eph receptor and/or anti-ephrin antibodies or antigen binding regions (U.S. Patent Nos. 5,981,245; 5,728,813; 5,969,110; 6,596,852; 6,232,447; 6,057,124; and patent family members thereof); anti-PDGF-BB antagonists (e.g., specifically binding antibodies or antigen binding regions) as well as antibodies or antigen binding regions specifically binding to PDGF-BB ligands, and PDGFR kinase inhibitory agents (e.g., antibodies or antigen binding regions that specifically bind thereto).

Exemplary anti-angiogenic/anti-tumor agents include, but are not limited to, SF-7784 (Pfizer, USA); cilengitide (Merck KgaA, Germany, EPO 770622); pegaptanib octasodium (Gilead Sciences, USA); Alphastatin (BioActa, UK); M-PGA (Celgene, USA, U.S. Pat. No. 5,712,291); ilomastat (Arriva, USA, U.S. Pat. No. 5,892,112); emaxanib (Pfizer, USA,.U.S. Pat. No. 5,792,783); vatalanib (Novartis, Switzerland); 2-methoxyestradiol (EntreMed, USA); TLC ELL-12 (Elan, Ireland); anecortave acetate (Alcon, USA); alpha-D148 Mab (Amgen, USA); CEP-7055 (Cephalon, USA); anti-Vn Mab (Crucell, Netherlands); DAC:antiangiogenic (ConjuChem, Canada); Angiocidin (InKine Pharmaceutical, USA); KM-2550 (Kyowa Hakko, Japan); SU-0879 (Pfizer, USA); CGP-79787 (Novartis, Switzerland, EP 970070); ARGENT technology (Ariad, USA); YIGSR-Strealth (Johnson & Johnson, USA); fibrinogen-E fragment (BioActa, UK); angiogenesis inhibitor (Trigen, UK); TBC-1635 (Encysive Pharmaceuticals, USA); SC-236 (Pfizer, USA); ABT-567 (Abbott, USA); Metastatin (EntreMed, USA); angiogenesis inhibitor (Tripep, Sweden); maspin (Sosei, Japan); 2-methoxyestradiol (Oncology Sciences Corporation, USA); ER-68203-00 (IVAX, USA); Benefin (Lane Labs, USA); Tz-93 (Tsumura, Japan); TAN-1 120 (Takeda, Japan); FR-111142 (Fujisawa, Japan, JP 02233610); platelet factor 4 (RepliGen, USA, EP 407122); vascular endothelial growth factor antagonist (Borean, Denmark); temsirolimus (CCI-779) (University of South Carolina, USA); bevacizumab (pINN) (Genentech, USA); angiogenesis inhibitors (SUGEN, USA); XL 784 (Exelixis, USA); XL 647 (Exelixis, USA); Mab, alpha5beta3 integrin, Vitaxin and second generation Vitaxin (Applied Molecular Evolution, USA and MedImmune USA); Retinostat® gene therapy (Oxford BioMedica, UK); enzastaurin hydrochloride (USAN) (Lilly, USA); CEP 7055 (Cephalon, USA and Sanofi-Synthelabo, France); BC 1 (Genoa Institute of Cancer Research, Italy); angiogenesis inhibitor (Alchemia, Australia); VEGF antagonist (Regeneron, USA); rBPI 21 and BPI-derived antiangiogenic (XOMA, USA); PI 88 (Progen, Australia); cilengitide (pINN) (Merck KgaA, Germany; Munich Technical University, Germany; Scripps Clinic and Research Foundation, USA); cetuximab (INN) (Aventis, France); AVE 8062 (Ajinomoto, Japan); AS 1404 (Cancer Research Laboratory, New Zealand); SG 292 (Telios, USA); Endostatin (Boston Children's Hospital, USA); 2-methoxyestradiol (Boston Childrens Hospital, USA); ZD 6474 (AstraZeneca, UK); ZD 6126 (Angiogene Pharmaceuticals, UK); PPI 2458 (Praecis, USA); AZD 9935 (AstraZeneca, UK); AZD 2171 (AstraZeneca, UK); vatalanib (pINN) (Novartis, Switzerland and Schering AG, Germany); tissue factor pathway inhibitors (EntraMed, USA); pegaptanib (Pinn) (Gilead Sciences, USA); xanthorrhizol (Yonsei University, South Korea); vaccine, gene-based, VEGF-2 (Scripps Clinic and Research Foundation, USA); SPV5.2 (Supratek, Canada); SDX 103 (University of California at San Diego, USA); PX 478 (Pro1X, USA); Metastatin (EntreMed, USA); troponin I (Harvard University, USA); SU 6668 (SUGEN, USA); OXI 4503 (OXiGENE, USA); o-guanidines (Dimensional Pharmaceuticals, USA); motuporamine C (British Columbia University, Canada); CDP 791 (Celltech Group, UK); atiprimod (pINN) (GlaxoSmithKline, UK); E 7820 (Eisai, Japan); CYC 381 (Harvard University, USA); AE 941 (Aeterna, Canada); FGF2 cancer vaccine (EntreMed, USA); urokinase plasminogen activator inhibitor (Dendreon, USA); oglufanide (pINN) (Melmotte, USA); HIF-1alfa inhibitors (Xenova, UK); CEP 5214 (Cephalon, USA); BAY RES 2622 (Bayer, Germany); Angiocidin (InKine, USA); A6 (Angstrom, USA); KR 31372 (Korean Research Institute of Chemical Technology, South Korea); GW 2286 (GlaxoSmithKline, UK); EHT 0101 (ExonHit, France); CP 868596 (Pfizer, USA); CP 564959 (OSI, USA); CP 547632 (Pfizer, USA); 786034 (GlaxoSmithKline, UK); KRN 633 (Kirin Brewery, Japan); drug delivery system, intraocular, 2-methoxyestradiol (EntreMed, USA); anginex (Maastricht University, Netherlands, and Minnesota University, USA); ABT 510 (Abbott, USA); AAL 993 (Novartis, Switzerland); VEGI (ProteomTech, USA); tumor necrosis factor-alpha inhibitors (National Institute on Aging, USA); SU 11248 (Pfizer, USA and SUGEN USA); ABT 518 (Abbott, USA); YH16 (Yantai Rongchang, China); S-3APG (Boston Childrens Hospital, USA and EntreMed, USA); Mab, KDR (ImClone Systems, USA); Mab, alpha5 beta1 (Protein Design, USA); KDR kinase inhibitor (Celltech Group, UK, and Johnson & Johnson, USA); GFB 116 (South Florida University, USA and Yale University, USA); CS 706 (Sankyo, Japan); combretastatin A4 prodrug (Arizona State University, USA); chondroitinase AC (IBEX, Canada); BAY RES 2690 (Bayer, Germany); AGM 1470 (Harvard University, USA, Takeda, Japan, and TAP, USA); AG 13925 (Agouron, USA); Tetrathiomolybdate (University of Michigan, USA); GCS 100 (Wayne State University, USA); CV 247 (Ivy Medical, UK); CKD 732 (Chong Kun Dang, South Korea); Mab, vascular endothelium growth factor (Xenova, UK); irsogladine (INN) (Nippon Shinyaku, Japan); RG 13577 (Aventis, France); WX 360 (Wilex, Germany); squalamine (pINN) (Genaera, USA); RPI 4610 (Sirna, USA); galacto fucan sulphate (Marinova, Australia); heparanase inhibitors (InSight, Israel); KL 3106 (Kolon, South Korea); Honokiol (Emory University, USA); ZK CDK (Shering AG, Germany); ZK Angio (Schering AG, Germany); ZK 229561 (Novartis, Switzerland, and Schering AG, Germany); XMP 300 (XOMA, USA); VGA 1102 (Taisho, Japan); VEGF receptor modulators (Pharmacopeia, USA); VE-cadherin-2 antagonists (ImClone Systems, USA); Vasostatin (National Institutes of Health, USA); vaccine, Flk-1 (ImClone Systems, USA); TZ 93 (Tsumura, Japan); TumStatin (Beth Israel Hospital, USA); truncated soluble FLT 1 (vascular endothelial growth factor receptor 1) (Merck & Co, USA); Tie-2 ligands (Regeneron, USA); and thrombospondin 1 inhibitor (Allegheny Health, Education and Research Foundation, USA).

Certain cancer therapy agents include, but are not limited to: thalidomide and thalidomide analogues (N-(2,6-dioxo-3-piperidyl)phthalimide); tecogalan sodium (sulfated polysaccharide peptidoglycan); TAN 1120 (8-acetyl-7,8,9,10-tetrahydro-6,8,11-trihydroxy-1-methoxy-10-[[octahydro-5-hydroxy-2-(2-hydroxypropyl)-4,10-dimethylpyrano[3,4-d]-1,3,6-dioxazocin-8-yl]oxy]-5,12-naphthacenedione); suradista (7,7'-[carbonylbis[imino(1-methyl-1H-pyrrole-4,2-diyl)carbonylimino(1-methyl-1H- pyrrole-4,2-diyl)carbonylimino]]bis-1,3-naphthalenedisulfonic acid tetrasodium salt); SU 302; SU 301; SU 1498 ((E)-2-cyano-3-[4-hydroxy-3,5-bis(1-methylethyl)phenyl]-N-(3-phenylpropyl)-2-pro penamide); SU 1433 (4-(6,7-dimethyl-2-quinoxalinyl)-1,2-benzenediol); ST 1514; SR 25989; soluble Tie-2; SERM derivatives; Pharmos; semaxanib (pINN)(3-[(3,5-dimethyl-1H-pyrrol-2-yl)methylene]-1,3-dihydro-2H-indol-2-one); S 836; RG 8803; RESTIN; R 440 (3-(1-methyl-1H-indol-3-yl)-4-(1-methyl-6-nitro-1H-indol-3-yl)-1H-pyrrole-2,5-dione); R 123942 (1-[6-(1,2,4-thiadiazol-5-yl)-3-pyridazinyl]-N-[3-(trifluoromethyl)phenyl]-4-piperidinamine); prolyl hydroxylase inhibitor; progression elevated genes; prinomastat (INN) ((S)-2,2-dimethyl-4-[[p-(4-pyridyloxy)phenyl]sulphonyl]-3-thiomorpholinecarbohydroxamic acid); NV 1030; NM 3 (8-hydroxy-6-methoxy-alpha-methyl-1-oxo-1H-2-benzopyran-3-acetic acid); NF 681; NF 050; MIG; METH 2; METH 1; manassantin B (alpha -[1-[4-[5-[4-[2-(3,4-dimethoxyphenyl)-2-hydroxy-1-methylethoxy]-3-methoxyphenyl]tetrahydro-3,4-dimethyl-2-furanyl]-2-methoxyphenoxy]ethyl]-1,3-benzodioxole-5-methanol); KDR monoclonal antibody; alpha5beta3 integrin monoclonal antibody; LY 290293 (2-amino-4-(3-pyridinyl)-4H -naphtho[1,2-b]pyran-3-carbonitrile); KP 0201448; KM 2550; integrin-specific peptides; INGN 401; GYKI 66475; GYKI 66462; greenstatin (101-354-plasminogen (human)); gene therapy for rheumatoid arthritis, prostate cancer, ovarian cancer, glioma, endostatin, colorectal cancer, ATF BTPI, antiangiogenesis genes, angiogenesis inhibitor, or angiogenesis; gelatinase inhibitor, FR 111142 (4,5-dihydroxy-2-hexenoic acid 5-methoxy-4-[2-methyl-3-(3-methyl-2-butenyl)oxiranyl]-1-oxaspiro[2.5] oct-6-yl ester); forfenimex (pINN) (S)-alpha-amino-3-hydroxy-4-(hydroxymethyl)benzeneacetic acid); fibronectin antagonist (1-acetyl-L-prolyl-L-h istidyl-L-seryl-L-cysteinyl-L-aspartamide); fibroblast growth factor receptor inhibitor; fibroblast growth factor antagonist; FCE 27164 (7,7'-[carbonylbis[imino(1-methyl-1H-pyrrole-4,2-diyl)carbonylimino(1-methyl-1H- pyrrole-4,2-diyl)carbonylimino]] bis-1,3,5-naphthalenetrisulfonic acid hexasodium salt); FCE 26752 (8,8'-[carbonylbis[imino(1-methyl-1H-pyrrole-4,2-diyl)carbonylimino(1-methyl-1H -pyrrole-4,2-diyl)carbonylimino]]bis-1,3,6-naphthalenetrisulfonic acid); endothelial monocyte activating polypeptide II; VEGFR antisense oligonucleotide; anti-angiogenic and trophic factors; ANCHOR angiostatic agent; endostatin; Del-1 angiogenic protein; CT 3577; contortrostatin; CM 101; chondroitinase AC; CDP 845; CanStatin; BST 2002; BST 2001; BLS 0597; BIBF 1000; ARRESTIN; apomigren (1304-1388-type XV collagen (human gene COL15A1 alpha1-chain precursor)); angioinhibin; aaATIII; A 36; 9alpha-fluoromedroxyprogesterone acetate ((6-alpha)-17-(acetyloxy)-9-fluoro-6-methyl-pregn-4-ene-3, 20-dione); 2-methyl-2-phthalimidino-glutaric acid (2-(1,3-dihydro-1-oxo-2H-isoindol-2-yl)-2-methylpentanedioic acid); Yttrium 90 labelled monoclonal antibody BC-1; Semaxanib (3-(4,5-Dimethylpyrrol-2-ylmethylene)indolin-2-one)(C15 H14 N2 O); PI 88 (phosphomannopentaose sulfate); Alvocidib (4H-1-Benzopyran-4-one, 2-(2-chlorophenyl)-5,7-dihydroxy-8-(3-hydroxy-1- methyl-4-piperidinyl)-cis-(-)-) (C21 H20 Cl N O5); E 7820; SU 11248 (5-[3-Fluoro-2-oxo-1,2-dihydroindol-(3Z)-ylidenemethyl]-2,4-dimethyl-1H-pyrrole-3-carboxylic acid (2-diethylaminoethyl)amide) (C22 H27 F N4 O2); Squalamine (Cholestane-7,24-diol, 3-[[3-[(4-aminobutyl) aminopropyl]amino]-, 24-(hydrogen sulfate), (3. beta.,5. alpha.,7. alpha.)-) (C34 H65 N3 O5 S); Eriochrome Black T; AGM 1470 (Carbamic acid, (chloroacetyl)-, 5-methoxy-4-[2-methyl-3-(3-methyl-2-butenyl)oxiranyl]-1-oxaspiro[2,5] oct-6-yl ester, [3R -[3alpha, 4alpha(2R, 3R), 5beta, 6beta]]) (C19 H28 Cl N O6); AZD 9935; BIBF 1000; AZD 2171; ABT 828; KS-interleukin-2; Uteroglobin; A 6; NSC 639366 (1-[3-(Diethylamino)-2-hydroxypropylamino]-4-(oxyran-2-ylmethylamino)anthraquinone fumarate) (C24 H29 N3 O4. C4 H4 O4); ISV 616; anti-ED-B fusion proteins; HUI 77; Troponin I; BC-1 monoclonal antibody; SPV 5.2; ER 68203; CKD 731 (3-(3,4,5-Trimethoxyphenyl)-2(E)-propenoic acid (3R, 4S,5S,6R)-4-[2(R)-methyl-3(R)-3(R)-(3-methyl-2-butenyl) oxiran-2-yl]-5-methoxy-1-oxaspiro[2.5]oct-6-yl ester) (C28 H38 O8); IMC-1C11; aaATIII; SC 7; CM 101; Angiocol; Kringle 5; CKD 732 (3-[4-[2-(Dimethylamino)ethoxy]phenyl]-2(E)-propenoic acid)(C29 H41 N O6); U 995; Canstatin; SQ 885; CT 2584 (1-[11-(Dodecylamino)-10-hydroxyundecyl]-3,7-dimethylxanthine)(C30 H55 N5 O3); Salmosin; EMAP II; TX 1920 (1-(4-Methylpiperazino)-2-(2-nitro-1H-1-imidazoyl)-1-ethanone) (C10 H15 N5 O3); Alpha-v Beta-x inhibitor; CHIR 11509 (N-(1-Propynyl)glycyl-[N-(2-naphthyl)]glycyl-[N-(carbamoylmethyl)]glycine bis(4-methoxyphenyl)methylamide)(C36 H37 N5 O6); BST 2002; BST 2001; B 0829; FR 111142; 4,5-Dihydroxy-2(E)-hexenoic acid (3R,4S, 5S, 6R)-4-[1(R),2(R)-epoxy-1,5-dimethyl-4-hexenyl]-5-methoxy-1-oxaspiro[2.5]octan-6-yl ester (C22 H34 O7); and kinase inhibitors including, but not limited to, N-(4-chlorophenyl)-4-(4-pyridinylmethyl)-1-phthalazinamine; 4-[4-[[[[4-chloro-3-(trifluoromethyl)phenyl]amino]carbonyl]amino]phenoxy]-N-methyl-2-pyridinecarboxamide; N-[2-(diethylamino)ethyl]-5-[(5-fluoro-1,2-dihydro-2-oxo-3H-indol-3-ylidene)methyl]-2,4-dimethyl-1H-pyrrole-3-carboxamide; 3-[(4-bromo-2,6-difluorophenyl)methoxy]-5-[[[[4-(1-pyrrolidinyl)butyl]amino]carbonyl]amino]-4-isothiazolecarboxamide; N-(4-bromo-2-fluorophenyl)-6-methoxy-7-[(1-methyl-4-piperidinyl)methoxy]-4-quinazolinamine; 3-[5,6,7,13-tetrahydro-9-[(1-methylethoxy)methyl]-5-oxo-12H-indeno[2,1-a]pyrrolo[3,4-c]carbazol-12-yl]propyl ester N,N-dimethyl-glycine; N-[5-[[[5-(1,1-dimethylethyl)-2-oxazolyl]methyl]thio]-2-thiazolyl]-4-piperidinecarboxamide; N-[3-chloro-4-[(3-fluorophenyl)methoxy]phenyl]-6-[5-[[[2-(methylsulfonyl)ethyl]amino]methyl]-2-furanyl]-4-quinazolinamine; 4-[(4-Methyl-1-piperazinyl)methyl]-N-[4-methyl-3-[[4-(3-pyridinyl)-2-pyrimidinyl]amino]-phenyl]benzamide; N-(3-chloro-4-fluorophenyl)-7-methoxy-6-[3-(4-morpholinyl)propoxy]-4-quinazolinamine; N-(3-ethynylphenyl)-6,7-bis(2-methoxyethoxy)-4-quinazolinamine; N-(3-((((2R)-1-methyl-2-pyrrolidinyl)methyl)oxy)-5-(trifluoromethyl)phenyl)-2-((3-(1,3-oxazol-5-yl)phenyl)amino)-3-pyridinecarboxamide; 2-(((4-fluorophenyl)methyl)amino)-N-(3-((((2R)-1-methyl-2-pyrrolidinyl)methyl)oxy)-5-(trifluoromethyl)phenyl)-3-pyridinecarboxamide; N-[3-(Azetidin-3-ylmethoxy)-5-trifluoromethyl-phenyl]-2-(4-fluoro-benzylamino)-nicotinamide; 6-fluoro-N-(4-(1-methylethyl)phenyl)-2-((4-pyridinylmethyl)amino)-3-pyridinecarboxamide; 2-((4-pyridinylmethyl)amino)-N-(3-(((2S)-2-pyrrolidinylmethyl)oxy)-5-(trifluoromethyl)phenyl)-3-pyridinecarboxamide; N-(3-(1,1-dimethylethyl)-1H-pyrazol-5-yl)-2-((4-pyridinylmethyl)amino)-3-pyridinecarboxamide; N-(3,3-dimethyl-2,3-dihydro-1-benzofuran-6-yl)-2-((4-pyridinylmethyl)amino)-3-pyridinecarboxamide; N-(3-((((2S)-1-methyl-2-pyrrolidinyl)methyl)oxy)-5-(trifluoromethyl)phenyl)-2-((4-pyridinylmethyl)amino)-3-pyridinecarboxamide; 2-((4-pyridinylmethyl)amino)-N-(3-((2-(1-pyrrolidinyl)ethyl)oxy)-4-(trifluoromethyl)phenyl)-3-pyridinecarboxamide; N-(3,3-dimethyl-2,3-dihydro-1H-indol-6-yl)-2-((4-pyridinylmethyl)amino)-3-pyridinecarboxamide; N-(4-(pentafluoroethyl)-3-(((2S)-2-pyrrolidinylmethyl)oxy)phenyl)-2-((4-pyridinylmethyl)amino)-3-pyridinecarboxamide; N-(3-((3-azetidinylmethyl)oxy)-5-(trifluoromethyl)phenyl)-2-((4-pyridinylmethyl)amino)-3-pyridinecarboxamide; N-(3-(4-piperidinyloxy)-5-(trifluoromethyl)phenyl)-2-((2-(3-pyridinyl)ethyl)amino)-3-pyridinecarboxamide; N-(4,4-dimethyl-1,2,3,4-tetrahydro-isoquinolin-7-yl)-2-(1H-indazol-6-ylamino)-nicotinamide; 2-(1H-indazol-6-ylamino)-N-[3-(1-methylpyrrolidin-2-ylmethoxy)-5-trifluoromethyl -phenyl]-nicotinamide; N-[1-(2-dimethylamino-acetyl)-3,3-dimethyl-2,3-dihydro-1H-indol-6-yl]-2-(1H-indazol-6-ylamino)-nicotinamide; 2-(1H-indazol-6-ylamino)-N-[3-(pyrrolidin-2-ylmethoxy)-5-trifluoromethyl-phenyl]-nicotinamide; N-(1-acetyl-3,3-dimethyl-2,3-dihydro-1H-indol-6-yl)-2-(1H-indazol-6-ylamino) -nicotinamide; N-(4,4-dimethyl-1-oxo-1,2,3,4-tetrahydro-isoquinolin-7-yl)-2-(1H -indazol-6-ylamino)-nicotinamide; N-[4-(tert-butyl)-3-(3-piperidylpropyl)phenyl][2-(1H-indazol-6-ylamino)(3-pyridyl)]carboxamide; N-[5-(tert-butyl)isoxazol-3-yl][2-(1H-indazol-6-ylamino)(3-pyridyl)]carboxamide; and N-[4-(tert-butyl)phenyl][2-(1H-indazol-6-ylamino) (3-pyridyl)]carboxamide, and kinase inhibitors disclosed in U.S. Pat. Nos. 6,258,812; 6,235,764; 6,630,500; 6,515,004; 6,713,485; 5,521,184; 5,770,599; 5,747,498; 5,990,141; U.S. Patent Application Publication No. US2003/0105091; and Patent Cooperation Treaty publication nos. WO01/37820; WO01/32651; WO02/68406; WO02/66470; WO02/55501; WO04/05279; WO04/07481; WO04/07458; WO04/09784; WO02/59110; WO99/45009; WO98/35958; WO00/59509; WO99/61422; WO00/12089; and WO00/02871, each of which publications are hereby incorporated by reference for any purpose.

In certain embodiments, an EGFr-specific binding agent may be used alone or with at least one additional therapeutic agent for the treatment of an EGFr-related cancer. In certain embodiments, an EGFr-specific binding agent is used in conjunction with a therapeutically effective amount of an additional therapeutic agent. Exemplary therapeutic agents that may be administered with an EGFr-specific binding agent include, but are not limited to, a member of the geldanamycin family of anisamycin antibiotics; a Pro-HGF; NK2; a c-Met peptide inhibitor; an antagonist of Grb2 Src homology 2; a Gab1 modulator; dominant-negative Src; a von-Hippel-Landau inhibitor, including, but not limited to, wortmannin; P13 kinase inhibitors, other anti-receptor therapies, a COX-2 inhibitor, Celebrex™, celecoxib, ViOxx™, rofecoxib; a vascular endothelial growth factor (VEGF), a VEGF modulator, a fibroblast growth factor (FGF), an FGF modulator, an epidermal growth factor (EGF); an EGF modulator; a keratinocyte growth factor (KGF), a KGF-related molecule, a KGF modulator; and a matrix metalloproteinase (MMP) modulator.

In certain embodiments, an EGFr-specific binding agent is used with particular therapeutic agents to treat various cancers. In certain embodiments, in view of the condition and the desired level of treatment, two, three, or more agents may be administered. Where the compounds are used with one or more other components, the compound and the one or more other components may be administered together, separately, or sequentially (e.g., in a pharmaceutical format). In certain embodiments, such agents may be provided together by inclusion in the same formulation. In certain embodiments, such agents and an EGFr-specific binding agent may be provided together by inclusion in the same formulation. In certain embodiments, such agents may be formulated separately and provided together by inclusion in a treatment kit. In certain embodiments, such agents and an EGFr-specific binding agent may be formulated separately and provided together by inclusion in a treatment kit. In certain embodiments, such agents may be provided separately.

In certain embodiments, when administered by gene therapy, the genes encoding protein agents and/or an EGFr-specific binding agent may be included in the same vector. In certain embodiments, the genes encoding protein agents and/or an EGFr-specific binding agent may be under the control of the same promoter region. In certain embodiments, the genes encoding protein agents and/or an EGFr-specific binding agent may be in separate vectors.

In certain embodiments, an EGFr-specific binding agent may be used to treat non-human animals, such as pets (dogs, cats, birds, primates, etc.), and domestic farm animals (horses cattle, sheep, pigs, birds, etc.). In certain such instances, an appropriate dose may be determined according to the animal's body weight. For example, in certain embodiments, a dose of 0.2-1 mg/kg may be used. In certain embodiments, the dose may be determined according to the animal's surface area, an exemplary dose ranging from 0.1 to 20 mg/in$^2$, or from 5 to 12 mg/m$^2$. For small animals, such as dogs or cats, in certain embodiments, a suitable dose is 0.4 mg/kg. In certain embodiments, EGFr-specific binding agents are administered by injection or other suitable route one or more times per week until the animal's condition is improved, or it may be administered indefinitely.

It is understood that the response by individual patients to the aforementioned medications or combination therapies may vary, and an appropriate efficacious combination of drugs for each patient may be determined by his or her physician.

The cynomolgus monkey provides a useful model for certain diseases. Exemplary diseases include, but are not limited to, transplantation rejection syndrome and inflammatory bowel disease-like disease. When testing the efficacy of a human monoclonal antibody in a cynomolgus monkey human disease model, in certain embodiments, it is useful to determine whether the EGFr-specific binding agent binds to EGFr in humans and cynomolgus monkeys at a comparable level.

In certain embodiments, an EGFr-specific binding agent may be part of a conjugate molecule comprising all or part of the EGFr-specific binding agent and a cytotoxic agent. The term "cytotoxic agent" refers to a substance that inhibits or prevents the function of cells and/or causes the death or destruction of cells. The term includes, but is not limited to, radioactive isotopes (e.g., $I^{131}$, $I^{125}$, $Y^{90}$ and $Re^{186}$), chemotherapeutic agents, and toxins such as enzymatically active toxins of bacterial, fungal, plant or animal origin, or fragments thereof. Exemplary cytotoxic agents include, but are hot limited to, Adriamycin, Doxorubicin, 5-Fluorouracil, Cytosine arabinoside ("Ara-C"), Cyclophosphamide, Thiotepa, Taxotere (docetaxel), Busulfan, Cytoxin, Taxol, Methotrexate, Cisplatin, Melphalan, Vinblastine, Bleomycin, Etoposide, Ifosfamide, Mitomycin C, Mitoxantrone, Vincreistine, Vinorelbine, Carboplatin, Teniposide, Daunomycin, Carminomycin, Aminopterin, Dactinomycin, Mitomycins, Esperamicins, Melphalan and other related nitrogen mustards.

In certain embodiments, an EGFr-specific binding agent may be part of a conjugate molecule comprising all or part of the EGFr-specific binding agent and a prodrug. In certain embodiments, the term "prodrug" refers to a precursor or derivative form of a pharmaceutically active substance. In certain embodiments, a prodrug is less cytotoxic to cells compared to the parent drug and is capable of being enzymatically activated or converted into the more active cytotoxic parent form. Exemplary prodrugs include, but are not limited to, phosphate-containing prodrugs, thiophosphate-containing prodrugs, sulfate-containing prodrugs, peptide-containing prod rugs, D-amino acid-modified prod rugs, glycosylated prodrugs, beta-lactam-containing prodrugs, optionally substituted phenoxyacetamide-containing prodrugs and optionally substituted phenylacetamide-containing prodrugs, 5-fluorocytosine and other 5-fluorouridine prodrugs which can be converted into a more active cytotoxic free drug. Examples of cytotoxic drugs that can be derivatized into a prodrug form include, but are not limited to, those cytotoxic agents described above. See, e.g., U.S. Pat. No. 6,702,705.

In certain embodiments, antibody conjugates function by having the antibody portion of the molecule target the cytotoxic portion or prodrug portion of the molecule to a specific population of cells in the patient. In the case of EGFr-specific binding agents, such conjugate molecules may be used, for example, in certain embodiments, to destroy abnormally proliferating cells, such as cancer cells.

In certain embodiments, methods of treating a patient comprising administering a therapeutically effective amount of an EGFr-specific binding agent are provided. In certain embodiments, methods of treating a patient comprising administering a therapeutically effective amount of an antibody conjugate are provided. In certain embodiments, an antibody is used in conjunction with a therapeutically effective amount of at least one additional therapeutic agent, as discussed above.

As discussed above, in certain embodiments, EGFr-specific binding agents may be administered concurrently with one or more other drugs that are administered to the same patient, each drug being administered according to a regimen suitable for that medicament. Such treatment encompasses pre-treatment, simultaneous treatment, sequential treatment, and alternating regimens. Additional examples of such drugs include, but are not limited to, antivirals, antibiotics, analgesics, corticosteroids, antagonists of inflammatory cytokines, DMARDs, nonsteroidal anti-inflammatories, chemotherapeutics, and stimulators of angiogenesis.

In certain embodiments, various medical disorders are treated with EGFr-specific binding agents in combination with a stimulator of apoptosis. For example, in certain embodiments, EGFr-specific binding agents may be administered in a composition that also contains a compound that stimulates apoptosis of one or more cells. In certain embodiments, the EGFr-specific binding agent and stimulators of apoptosis may be administered as separate compositions, and these may be administered by the same or different routes.

In certain embodiments, pharmaceutical compositions are provided comprising a therapeutically effective amount of an EGFr-specific binding agent and a pharmaceutically acceptable diluent, carrier, solubilizer, emulsifier, preservative and/or adjuvant.

In certain embodiments, pharmaceutical compositions are provided comprising a therapeutically effective amount of an EGFr-specific binding agent and a therapeutically effective amount of at least one additional therapeutic agent, and a pharmaceutically acceptable diluent, carrier, solubilizer, emulsifier, preservative and/or adjuvant.

In certain embodiments, acceptable formulation materials preferably are nontoxic to recipients at the dosages and concentrations employed.

In certain embodiments, the pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. In certain embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. (*Remington's Pharmaceutical Sciences*, 18$_{th}$ Edition, A. R. Gennaro, ed., Mack Publishing Company (1990).

In certain embodiments, an EGFr-specific binding agent and/or an additional therapeutic molecule is linked to a half-life extending vehicle known in the art. Such vehicles include, but are not limited to, the Fc domain, polyethylene glycol, and dextran. Such vehicles are described, e.g., in U.S. Pat. No. 6,660,843 and published PCT Application No. WO 99/25044.

In certain embodiments, the optimal pharmaceutical composition will be determined by one skilled in the art depending upon, for example, the intended route of administration, delivery format and desired dosage. See, for example, *Remington's Pharmaceutical Sciences*, supra. In certain embodiments, such compositions may influence the physical state, stability, rate of in vivo release and rate of in vivo clearance of the EGFr-specific binding agents.

In certain embodiments, the primary vehicle or carrier in a pharmaceutical composition may be either aqueous or non-aqueous in nature. For example, in certain embodiments, a suitable vehicle or carrier may be water for injection, physiological saline solution or artificial cerebrospinal fluid, possibly supplemented with other materials common in compositions for parenteral administration. In certain embodiments, neutral buffered saline or saline mixed with serum albumin are further exemplary vehicles. In certain embodiments, pharmaceutical compositions comprise Tris buffer of about pH 7.0-8.5, or acetate buffer of about pH 4.0-5.5, which may further include sorbitol or a suitable substitute therefor. In certain embodiments, a pharmaceutical composition is an aqueous or liquid formulation comprising an acetate buffer of about pH 4.0-5.5, a polyol (polyalcohol), and optionally, a surfactant, wherein the composition does not comprise a salt, e.g., sodium chloride, and wherein the composition is isotonic for the patient. Exemplary polyols include, but are not limited to, sucrose, glucose, sorbitol, and mannitol. An exemplary surfactant includes, but is not limited to, polysorbate. In certain embodiments, a pharmaceutical composition is an aqueous or liquid formulation comprising an acetate buffer of about pH 5.0, sorbitol, and a polysorbate, wherein the composition does not comprise a salt, e.g., sodium chloride, and wherein the composition is isotonic for the patient. Certain exemplary compositions are found, for example, in U.S. Pat. No. 6,171,586. Additional pharmaceutical carriers include, but are not limited to, oils, including petroleum oil, animal oil, vegetable oil, peanut oil, soybean oil, mineral oil, sesame oil, and the like. In certain embodiments, aqueous dextrose and glycerol solutions can also be employed as liquid carriers, particularly for injectable solutions. In certain embodiments, a composition comprising an antibody, with or without at least one additional therapeutic agent, may be prepared for storage by mixing the selected composition having the desired degree of purity with optional formulation agents (*Remington's Pharmaceutical Sciences*, supra) in the form of a lyophilized cake or an aqueous solution. Further, in certain embodiments, a composition comprising an antibody, with or without at least one additional therapeutic agent, may be formulated as a lyophilizate using appropriate excipient solutions (e.g., sucrose) as diluents.

In certain embodiments, an EGFr-specific binding agent is administered in the form of a physiologically acceptable composition comprising purified recombinant protein in conjunction with physiologically acceptable carriers, excipients or diluents. In certain embodiments, such carriers are non-toxic to recipients at the dosages and concentrations employed. In certain embodiments, preparing such compositions may involve combining the EGFr-specific binding agent with buffers, antioxidants such as ascorbic acid, low molecular weight polypeptides (such as those having fewer than 10 amino acids), proteins, amino acids, carbohydrates such as glucose, sucrose or dextrins, chelating agents such as EDTA, glutathione and/or other stabilizers, and excipients. In certain embodiments, appropriate dosages are determined in standard dosing trials, and may vary according to the chosen route of administration. In certain embodiments, in accordance with appropriate industry standards, preservatives may also be added, which include, but are not limited to, benzyl alcohol. In certain embodiments, the amount and frequency of administration may be determined based on such factors as the nature and severity of the disease being treated, the desired response, the age and condition of the patient, and so forth.

In certain embodiments, pharmaceutical compositions can be selected for parenteral delivery. The preparation of certain such pharmaceutically acceptable compositions is within the skill of the art.

In certain embodiments, the formulation components are present in concentrations that are acceptable to the site of administration. In certain embodiments, buffers are used to maintain the composition at physiological pH or at a slightly lower pH, typically within a pH range of from about 5 to about 8.

In certain embodiments, when parenteral administration is contemplated, a therapeutic composition may be in the form of a pyrogen-free, parenterally acceptable aqueous solution comprising the desired antibody, with or without additional therapeutic agents, in a pharmaceutically acceptable vehicle. In certain embodiments, a vehicle for parenteral injection is sterile distilled water in which the antibody, with or without at least one additional therapeutic agent, is formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads, or liposomes, that may provide for the controlled or sustained release of the product which may then be delivered via a depot injection. In certain embodiments, hyaluronic acid may also be used, and may have the effect of promoting sustained duration in the circulation. In certain embodiments, implantable drug delivery devices may be used to introduce the desired molecule.

In certain embodiments, a pharmaceutical composition may be formulated for inhalation. In certain embodiments, an EGFr-specific binding agent, with or without at least one additional therapeutic agent, may be formulated as a dry powder for inhalation. In certain embodiments, an inhalation solution comprising an EGFr-specific binding agent, with or without at least one additional therapeutic agent, may be formulated with a propellant for aerosol delivery. In certain embodiments, solutions may be nebulized. Pulmonary administration is further described in PCT Publication No. WO94/20069, which describes pulmonary delivery of chemically modified proteins.

In certain embodiments, it is contemplated that formulations may be administered orally. In certain embodiments, an EGFr-specific binding agent, with or without at least one additional therapeutic agent, that is administered in this fashion may be formulated with or without those carriers customarily used in the compounding of solid dosage forms such as tablets and capsules. In certain embodiments, a capsule may be designed to release the active portion of the formulation at the point in the gastrointestinal tract when bioavailability is maximized and pre-systemic degradation is minimized. In certain embodiments, at least one additional agent can be included to facilitate absorption of the EGFr-specific binding agent and/or any additional therapeutic agents. In certain embodiments, diluents, flavorings, low melting point waxes, vegetable oils, lubricants, suspending agents, tablet disintegrating agents, and/or binders may also be employed.

In certain embodiments, a pharmaceutical composition may involve an effective quantity of an EGFr-specific binding agent, with or without at least one additional therapeutic agent, in a mixture with non-toxic excipients which are suitable for the manufacture of tablets. In certain embodiments, by dissolving the tablets in sterile water, or another appropriate vehicle, solutions may be prepared in unit-dose form. Suitable excipients include, but are not limited to, inert diluents, such as calcium carbonate, sodium carbonate or bicarbonate, lactose, or calcium phosphate; and binding agents, such as starch, gelatin, and acacia; and lubricating agents such as magnesium stearate, stearic acid, and talc.

Additional pharmaceutical compositions will be evident to those skilled in the art, including formulations involving an EGFr-specific binding agent, with or without at least one additional therapeutic agent, in sustained- or controlled-delivery formulations. In certain exemplary sustained- or controlled-delivery formulations include, but are not limited to, liposome carriers, bio-erodible microparticles, porous beads, and depot injections. Certain exemplary techniques for preparing certain formulations are known to those skilled in the art. See for example, PCT publication no. WO93/15722, which-describes the controlled release of porous polymeric microparticles for the delivery of pharmaceutical compositions. In certain embodiments, sustained-release preparations may include semipermeable polymer matrices in the form of shaped articles, e.g. films, or microcapsules. Sustained release matrices include, but are not limited to, polyesters, hydrogels, polylactides (U.S. Pat. No. 3,773,919 and EP 058, 481), copolymers of L-glutamic acid and gamma ethyl-L-glutamate (Sidman et al., *Biopolymers*, 22:547-556 (1983)), poly (2-hydroxyethyl-methacrylate) (Langer et al., *J. Biomed. Mater. Res.*, 15:167-277 (1981) and Langer, *Chem. Tech.*, 12:98-105 (1982)), ethylene vinyl acetate (Langer et al., supra), and poly-D(−)-3-hydroxybutyric acid (EP 133,988). In certain embodiments, sustained release compositions may also include liposomes, which can be prepared, in certain embodiments, by any of several methods known in the art. See e.g., Eppstein et al., *Proc. Natl. Acad. Sci. USA*, 82:3688-3692 (1985); EP 036,676; EP 088,046 and EP 143,949.

In certain embodiments, the pharmaceutical composition to be used for in vivo administration is sterile. In certain embodiments, the pharmaceutical composition to be used for in vivo administration is made sterile by filtration through sterile filtration membranes. In certain embodiments, where the composition is lyophilized, sterilization using sterile filtration membranes may be conducted either prior to or following lyophilization and reconstitution. In certain embodiments, the composition for parenteral administration may be stored in lyophilized form or in a solution. In certain embodiments, parenteral compositions generally are placed into a container having a sterile access port, for example, an intravenous solution bag or vial having a stopper pierceable by a hypodermic injection needle.

In certain embodiments, after the pharmaceutical composition has been formulated, it may be stored in sterile vials as a solution, suspension, gel, emulsion, solid, or as a dehydrated or lyophilized powder. In certain embodiments, such formulations may be stored either in a ready-to-use form or in a form (e.g., a lyophilized form) that is reconstituted prior to administration.

In certain embodiments, kits for producing a single-dose administration unit are provided. In certain embodiments, the kits may each contain both a first container having a dried protein and a second container having an aqueous formulation. In certain embodiments, kits containing single and/or multi-chambered pre-filled syringes (e.g., liquid syringes and lyosyringes) are included.

In certain embodiments, the effective amount of a pharmaceutical composition comprising an EGFr-specific binding agent, with or without at least one additional therapeutic agent, to be employed therapeutically will depend, for example, upon the therapeutic context and objectives. One skilled in the art will appreciate that the appropriate dosage levels for treatment, according to certain embodiments, will thus vary depending, in part, upon the molecule delivered, the indication for which the EGFr-specific binding agent, with or without at least one additional therapeutic agent, is being used, the route of administration, and the size (body weight, body surface or organ size) and/or condition (the age and general health) of the patient. In certain embodiments, the clinician may titer the dosage and modify the route of administration to obtain the optimal therapeutic effect. In certain embodiments, a typical dosage may range from about 0.1 µg/kg to up to about 100 mg/kg or more, depending on the factors mentioned above. In certain embodiments, the dosage may range from 0.1 µg/kg up to about 100 mg/kg; or 1 µg/kg up to about 100 mg/kg; or 5 µg/kg up to about 100 mg/kg.

In certain embodiments, the frequency of dosing will take into account the pharmacokinetic parameters of the EGFr-specific binding agent and/or any additional therapeutic agents in the formulation used. In certain embodiments, a clinician will administer the composition until a dosage is reached that achieves the desired effect. In certain embodiments, the composition may therefore be administered as a single dose, or as two or more doses (which may or may not contain the same amount of the desired molecule) over time, or as a continuous infusion via an implantation device or catheter. Certain methods of further refining the appropriate dosage are within the skill in the art. In certain embodiments, appropriate dosages may be ascertained through use of appropriate dose-response data.

In certain embodiments, the route of administration of the pharmaceutical composition is in accord with known methods, e.g. orally, through injection by intravenous, intraperitoneal, intracerebral (intra-parenchymal), intracerebroventricular, intramuscular, intra-ocular, intraarterial, intraportal, or intralesional routes; by sustained release systems or by implantation devices. In certain embodiments, the compositions may be administered by bolus injection or continuously by infusion, or by implantation device.

As discussed above, in various embodiments, any efficacious route of administration may be used to administer an EGFr-specific binding agent. If injected, in certain embodiments, an EGFr-specific binding agent may be administered, for example, via intra-articular, intravenous, intramuscular, intralesional, intraperitoneal, intracranial, intranasal, inhalation or subcutaneous routes by bolus injection or by continuous infusion. Exemplary methods of administration include, but are not limited to, sustained release from implants, aerosol inhalation, eyedrops, oral preparations, including pills, syrups, lozenges, and chewing gum, and topical preparations such as lotions, gels, sprays, ointments, and other suitable techniques.

In certain embodiments, administration by inhalation is beneficial when treating diseases associated with pulmonary disorders. In certain embodiments, an EGFr-specific binding agent may be administered by implanting cultured cells that express an EGFr-specific binding agent. In certain embodiments, the patient's own cells are induced to produce by transfection in vivo or ex vivo with one or more vectors that encode an EGFr-specific binding agent. In certain embodiments, this vector can be introduced into the patient's cells, for example, by injecting naked DNA or liposome-encapsulated DNA that encodes an EGFr-specific binding agent, or by other methods of transfection. When an EGFr-specific binding agent is administered in combination with one or more other biologically active compounds, in certain embodiments, these may be administered by the same or by different routes, and may be administered together, separately, or sequentially.

In certain embodiments, the composition may be administered locally via implantation of a membrane, sponge or another appropriate material onto which the desired molecule has been absorbed or encapsulated. In certain embodiments, where an implantation device is used, the device may be implanted into any suitable tissue or organ, and delivery of the desired molecule may be via diffusion, timed-release bolus, or continuous administration.

In certain embodiments, it may be desirable to use a pharmaceutical composition comprising an EGFr-specific binding agent, with or without at least one additional therapeutic agent, in an ex vivo manner. In such embodiments, cells, tissues and/or organs that have been removed from the patient are exposed to a pharmaceutical composition comprising an antibody, with or without at least one additional therapeutic agent, after which the cells, tissues and/or organs are subsequently implanted back into the patient.

In certain embodiments, an EGFr-specific binding agent and any additional therapeutic agents can be delivered by implanting certain cells that have been genetically engineered, using methods such as those described herein, to express and secrete the polypeptides. In certain embodiments, such cells may be animal or human cells, and may be autologous, heterologous, or xenogeneic. In certain embodiments, the cells may be immortalized. In certain embodiments, in order to decrease the chance of an immunological response, the cells may be encapsulated to avoid infiltration of surrounding tissues. In certain embodiments, the encapsulation materials are typically biocompatible, semi-permeable polymeric enclosures or membranes that allow the release of the protein product(s) but prevent the destruction of the cells by the patient's immune system or by other detrimental factors from the surrounding tissues.

Certain Exemplary Methods

In certain embodiments, a method of predicting whether an EGFr-specific binding agent treatment will be efficacious in treating an EGFr-related cancer in a subject is provided. In certain embodiments, the method comprises determining the EGFr gene copy number in a sample from the subject. In certain embodiments, the presence of an increased EGFr gene copy number in the sample predicts that an EGFr-specific binding agent treatment will be efficacious in treating an EGFr-related cancer in the subject. In certain embodiments, the EGFr-specific binding agent treatment comprises an anti-EGFr antibody. In certain embodiments, the anti-EGFr antibody is a human anti-EGFr antibody. In certain embodiments, the anti-EGFr antibody is panitumumab. In certain embodiments, the EGFr-specific binding agent treatment comprises an EGFr-specific binding agent and at least one chemotherapeutic agent. In certain embodiments, the EGFr-related cancer is a solid tumor. In certain embodiments, the solid tumor comprises at least one cancer selected from colorectal cancer, lung cancer, breast cancer, ovarian cancer, prostate cancer, kidney cancer, and head and neck cancer.

In certain embodiments, determining the EGFr gene copy number in the sample comprises comparing the EGFr gene copy number in the sample to the EGFr gene copy number in a normal reference sample. In certain embodiments, the normal reference sample is from the same subject as the sample. In certain embodiments, the normal reference sample is not from the same subject as the sample. In certain embodiments, the normal reference sample is from the same tissue as the sample. In certain such embodiments, the normal reference sample is from nontumorigenic tissue and the sample is from tumorigenic tissue. In certain such embodiments, the normal reference sample is from non-malignant tissue and the sample is from malignant tissue. In certain embodiments, determining the EGFr gene copy number comprises fluorescent in situ hybridization analysis. In certain embodiments, determining the EGFr gene copy number comprises quantitative PCR. In certain embodiments, determining the EGFr gene copy number comprises Southern blot analysis. In certain embodiments, determining the EGFr gene copy number comprises another gene copy number determination methodology described herein. In certain embodiments, the EGFr-specific binding agent treatment comprises an anti-EGFr antibody. In certain embodiments, the anti-EGFr antibody is a human anti-EGFr antibody. In certain embodiments, the anti-EGFr antibody is panitumumab. In certain embodiments, the EGFr-specific binding agent treatment comprises an EGFr-specific binding agent and at least one chemotherapeutic agent. In certain embodiments, the EGFr-related cancer is a solid tumor. In certain embodiments, the solid tumor comprises at least one cancer selected from colorectal cancer, lung cancer, breast cancer, -ovarian cancer, prostate cancer, kidney cancer, and head and neck cancer.

In certain embodiments, determining the EGFr gene copy number in the sample comprises determining the EGFr gene copy number in a test sample from a tumor in the subject, determining the copy number of at least one reference nucleotide sequence in the test sample, and comparing the EGFr gene copy number in the test sample to the copy number of at least one reference nucleotide sequence in the test sample. In certain embodiments, an increased copy number of the EGFr gene in the test sample relative to the copy number of the at least one reference nucleotide sequence predicts that an EGFr-specific binding agent treatment will be efficacious in treating an EGFr-related cancer in the subject. In certain embodiments, the at least one reference nucleotide sequence is located on the same chromosome as an EGFr gene. In certain embodiments, the at least one reference nucleotide sequence is located on another chromosome from the chromosome where EGFr is located. In certain embodiments, the copy number of the at least one reference nucleotide sequence is two copies per cell. In certain embodiments, the at least one reference nucleotide sequence is a centromeric sequence. In certain embodiments, the ratio of the EGFr gene copy number to the copy number of the at least one reference nucleotide sequence in a normal sample is 1. In certain embodiments, determining the EGFr gene copy number and the at least one reference nucleotide sequence copy number comprises fluorescent in situ hybridization analysis. In certain embodiments, determining the EGFr gene copy number and the at least one reference nucleotide sequence copy number comprises quantitative PCR. In certain embodiments, determining the EGFr gene copy number and the at least one reference nucleotide sequence copy number comprises Southern blot analysis. In certain embodiments, determining the EGFr gene copy number and the at least one reference nucleotide sequence copy number comprises another gene copy number determination methodology described herein. In certain embodiments, the EGFr-related cancer is a solid tumor. In certain embodiments, the solid tumor comprises at least one cancer selected from colorectal cancer, lung cancer, breast cancer, ovarian cancer, prostate cancer, kidney cancer, and head and neck cancer. In certain embodiments, the EGFr-specific binding agent treatment comprises an anti-EGFr antibody. In certain embodiments, the anti-EGFr antibody is a human anti-EGFr antibody. In certain embodiments, the anti-EGFr antibody is panitumumab. In certain embodiments, the EGFr-specific binding agent treatment comprises an EGFr-specific binding agent and at least one chemotherapeutic agent.

In certain embodiments, determining the EGFr gene copy number comprises: determining the EGFr gene copy number in a test sample from the subject; determining the number of nuclei in the test sample; and comparing the EGFr gene copy number to the number of nuclei. In certain such embodiments, a ratio between the EGFr gene copy number and the number of nuclei of greater than two predicts that an EGFr-specific binding agent treatment will be efficacious in treating an EGFr-related cancer in the subject. In certain embodiments, the ratio of the EGFr gene copy number to the number of nuclei in a normal sample is 2. In certain embodiments, an increased EGFr gene copy number in a sample is indicated by a ratio of the EGFr gene copy number to the number of nuclei of greater than 2. In certain embodiments, the EGFr-specific binding agent treatment comprises an anti-EGFr antibody. In certain embodiments, the anti-EGFr antibody is a human anti-EGFr antibody. In certain embodiments, the anti-EGFr antibody is panitumumab. In certain embodiments, the EGFr-specific binding agent treatment comprises an EGFr-specific binding agent and at least one chemotherapeutic agent. In certain embodiments, the EGFr-related cancer is a solid tumor. In certain embodiments, the solid tumor comprises at least one cancer selected from colorectal cancer, lung cancer, breast cancer, ovarian cancer, prostate cancer, kidney cancer, and head and neck cancer.

In certain embodiments, determining the EGFr gene copy number and the number of nuclei comprises fluorescent in situ hybridization analysis. In certain embodiments, determining the EGFr gene copy number and the number of nuclei comprises quantitative PCR. In certain embodiments, determining the EGFr gene copy number and the number of nuclei comprises Southern blot analysis. In certain embodiments, determining the EGFr gene copy number and the number of nuclei comprises another gene copy number determination methodology described herein. In certain embodiments, the EGFr-related cancer is a solid tumor. In certain embodiments, the solid tumor comprises at least one cancer selected from colorectal cancer, lung cancer, breast cancer, ovarian cancer, prostate cancer, kidney cancer, and head and neck cancer. In certain embodiments, the EGFr-specific binding agent treatment comprises an anti-EGFr antibody. In certain embodiments, the anti-EGFr antibody treatment comprises a human anti-EGFr antibody. In certain embodiments, the anti-EGFr antibody is panitumumab. In certain embodiments, the EGFr-specific binding agent treatment comprises an EGFr-specific binding agent and at least one chemotherapeutic agent.

In certain embodiments, a method of treating a subject having an EGFr-related cancer is provided, comprising: determining the EGFr gene copy number in a sample from the subject, determining whether there is an increased EGFr gene copy number in the sample; and if there is an increased EGFr gene copy number in the sample, administering to the subject a pharmaceutically effective amount of an EGFr-specific binding agent. In certain embodiments, the EGFr-specific binding agent is an anti-EGFr antibody. In certain embodiments, the anti-EGFr antibody is a human anti-EGFr antibody. In certain embodiments, the anti-EGFr antibody is panitumumab. In certain embodiments, the EGFr-specific binding agent treatment comprises an EGFr-specific binding agent and at least one chemotherapeutic agent. In certain embodiments, determining the EGFr gene copy number comprises fluorescent in situ hybridization analysis. In certain embodiments, determining the EGFr gene copy number comprises quantitative PCR. In certain embodiments, determining the EGFr gene copy number comprises Southern blot analysis. In certain embodiments, determining the EGFr gene copy number comprises another gene copy number determination methodology described herein. In certain embodiments, the EGFr-related cancer is a solid tumor. In certain embodiments, the solid tumor comprises at least one cancer selected from colorectal cancer, lung cancer, breast cancer, ovarian cancer, prostate cancer, kidney cancer, and head and neck cancer.

In certain embodiments, a method of determining the efficacy of a treatment in a patient is provided, comprising: (a) determining the EGFr gene copy number in a first sample obtained from a patient to obtain a first EGFr gene copy number level; (b) administering the treatment to the patient; (c) determining the EGFr gene copy number in a second sample from the patient at a time following administration of the treatment, thereby generating a second EGFr gene copy number level; and (d) comparing the first and second EGFr gene copy number levels, wherein a decrease in the EGFr gene copy number in the second EGFr gene copy number level relative to the first EGFr gene copy number level indicates that the treatment is effective in the patient. In certain embodiments, determining the EGFr gene copy number comprises fluorescent in situ hybridization analysis. In certain embodiments, determining the EGFr gene copy number comprises quantitative PCR. In certain embodiments, determining the EGFr gene copy number comprises Southern blot analysis. In certain embodiments, determining the EGFr gene copy number comprises another gene copy number determination methodology described herein. In certain embodiments, the treatment comprises an EGFr-specific binding agent. In certain embodiments, the EGFr-specific binding agent is an anti-EGFr antibody. In certain embodiments, the anti-EGFr antibody is a human anti-EGFr antibody. In certain embodiments, the anti-EGFr antibody is panitumumab. In certain embodiments, the treatment comprises an EGFr-specific binding agent and at least one chemotherapeutic agent. In certain embodiments, the treatment is for an EGFr-related cancer. In certain embodiments, the EGFr-related cancer is a solid tumor. In certain embodiments, the solid tumor comprises at least one cancer selected from colorectal cancer, lung cancer, breast cancer, ovarian cancer, prostate cancer, kidney cancer, and head and neck cancer.

The following examples, including the experiments conducted and results achieved are provided for illustrative purposes only and are not to be construed as limiting upon the present invention.

EXAMPLES

Example 1

Isolation of CRC Tumor Samples and Correlation with Panitumumab Treatment

Ten patients were selected from patients enrolled at Ospedale Niguarda Ca'Granda for a panitumumab (human IgG2 monoclonal antibody to EGFr; Amgen Inc.) clinical trial for the treatment of EGFr-expressing colorectal cancer ("CRC"). Treatment protocols were approved by the Institutional Ethics Committee. Patients gave written informed consent for receiving panitumumab, as well as for analysis of tumor-expressed EGFr and molecules involved in EGFr activation. All ten patients were resistant to prior chemotherapy regimens. Those prior chemotherapy regimens are shown in Table 1 below. Patient tumor samples were assessed for EGFr expression using the EGFRPharmDX kit (DAKO Corp.) according to the manufacturer's instructions. All patients selected for the study had EGFr-expressing metastatic CRC, ascertained by the presence of EGFr staining in at least 1% of malignant cells. Patients were treated intravenously with panitumumab at a dose of 6 mg/kg every two weeks until disease progression was observed.

Tumor response to panitumumab treatment was evaluated by Computed Tomography Imaging ("CT scan") employing Response Evaluation Criteria in Solid Tumors (RECIST) criteria by institutional as well as independent radiologists according to clinical protocols. RECIST provides guidelines for identifying improvement, stable disease, or progressive disease based on tumor size (see Therasse et al., February 2000, "New Guidelines to Evaluate the Response to Treatment in Solid Tumors," J. Natl. Cancer Inst. 92(3): 205-216). The results of the RECIST analysis of patients treated with panitumumab are shown in Table 1.

TABLE 1

Relevant Clinical Characteristics of Patients Treated with Panitumumab

| Patient | Sex | Age | Number and Type of Prior Chemotherapy Regimens | Tumor Response to Panitumumab | Duration of Response (weeks) |
|---|---|---|---|---|---|
| 1 - 30624793 | M | 59 | 3: FOLFOX*, Capecitabine, FOLFIRI‡ | Partial Response | 33 |
| 2 - 2350661 | F | 62 | 2: FOLFOX, FOLFIRI | Partial Response | 24 |
| 3 - 30640715 | M | 57 | 2: FOLFIRI, FOLFOX | Partial Response | 16 |
| 4 - 30398321 | F | 78 | 3: FOLFOX, Capecitabine, FOLFIRI | Partial Response | 12+ |
| 5 - 10015851 | F | 52 | 4: FOLFOX, Irinotecan, Capecitabine, FOLFIRI | Stable Disease | 32 |
| 6 - 30656334 | M | 71 | 2: FOLFOX, FOLFIRI | Stable Disease | 16+ |
| 7 - 30667900 | M | 56 | 1: Oxaliplatin-Irinotecan-5-FU/FA | Progressive Disease | (no response) |
| 8 - 30384032 | F | 67 | 2: FOLFOX, FOLFIRI | Progressive Disease | (no response) |
| 9 - 30692441 | M | 54 | 2: FOLFOX, FOLFIRI | Progressive Disease | (no response) |
| 10 - 30685324 | F | 65 | 3: 5-FU/FA, FOLFOX, FOLFIRI | Progressive Disease | (no response) |

*FOLFOX is a combination of 5-fluorouracil, leucovorin, and oxaliplatin
‡FOLFIRI is a combination of 5-fluorouracil, leucovorin, and irinotecan Thus, six of the ten patients responded positively to the panitumumab treatment, showing either stable disease or a partial response.

Example 2

Mutational Analysis of EGFr, PI3K, Ras, and Raf in CRC Tumor Samples

Prior to initiation of panitumumab treatment discussed in Example 1, CRC tumor samples from each patient were embedded in paraffin. A 10 micron section was prepared from each patient sample. Regions of the section displaying tumor tissue were marked and the tissue was extracted with 0.2M NaOH/1 mM EDTA. Samples were subsequently neutralized with 100 mM Tris-TE. After extraction and neutralization, DNA from each sample was purified using a PCR Purification Kit (Qiagen) following the manufacturer's instructions.

Exon-specific PCR primers and sequencing primers were designed using the program Primer3 (Rozen S, Skaletsky H (2000) *Primer3 on the WWW for general users and for biologist programmers*. In: Krawetz, S., Misener, S. (eds) Bioinformatics Methods and Protocols: Methods in Molecular Biology. Humana Press, Totowa, N.J., pp 365-386). The designed primers were synthesized by Invitrogen™ (Carlsbad, Calif.). The forward PCR primer for EGFr exon 18 was GCTGAGGTGACCCTTGTCTC (SEQ ID NO: 1), the reverse PCR primer for EGFr exon 18 was ACAGCTTGCAAGGACTCTGG (SEQ ID NO: 2), and the sequencing primer for EGFr exon 18 was TGGAGCCTCTTACACCCAGT (SEQ ID NO: 3). The forward PCR primer for EGFr exon 19 was CCCAGTGTCCCTCACCTTC (SEQ ID NO: 4), the reverse PCR primer for EGFr exon 19 was CCACACAGCAAAGCAGAAAC (SEQ ID NO: 5), and the sequencing primer for EGFr exon 19 was GCTGGTAACATCCACCCAGA (SEQ ID NO: 6). The forward PCR primer for EGFr exon 21 was TGATCTGTCCCTCACAGCAG (SEQ ID NO: 7), the reverse PCR primer for EGFr exon 21 was TCAGGAAAATGCTGGCTGAC (SEQ ID NO: 8), and the sequencing primer for EGFr exon 21 was TTCAGGGCATGAACTACTTGG (SEQ ID NO: 9). The forward PCR primer for PI3K exon 9 was GGGAAAAATATGACAAAGAAAGC (SEQ ID NO: 10), the reverse PCR primer for PI3K exon 9 was CTGAGATCAGCCAAATTCAGTT (SEQ ID NO: 11), and the sequencing primer for PI3K exon 9 was TAGCTAGAGACAATGAATTAAGGGAAA (SEQ ID NO: 12). The forward PCR primer for PI3K exon 20 was CTCAATGATGCTTGGCTCTG (SEQ ID NO: 13), the reverse PCR primer for PI3K exon 20 was TGGAATCCAGAGTGAGCTTTC (SEQ ID NO: 14), and the sequencing primer for PI3K exon 20 was TTGATGACATTGCATACATTCG (SEQ ID NO: 15). The forward PCR primer for Ras exon 2 was GGTGGAGTATTTGATAGTGTATTAAC (SEQ ID NO: 16), the reverse PCR primer for Ras exon 2 was AGAATGGTCCTGCACCAGTAA (SEQ ID NO: 17), and the sequencing primer for Ras exon 2 was TCATTATTTTTATTATAAGGCCTGCTG (SEQ ID NO: 18). The forward PCR primer for B-Raf exon 15 was TGCTTGCTCTGATAGGAAAATG (SEQ ID NO: 19), the reverse PCR primer for B-Raf exon 15 was AGCATCTCAGGGCCAAAAAT (SEQ ID NO: 20), and the sequencing primer for B-Raf exon 15 was TGTTTTCCTTTACTTACTACACCTCA (SEQ ID NO: 21).

EGFr exons 18, 19, and 21, PI3K exons 9 and 20, Ras exon 2, and B-Raf exon 15 were amplified by PCR from the purified tumor genomic DNA using the PCR primers described above. PCR was performed in a total volume of 20 μL using a touchdown PCR program. The amplification program was as follows: 94° C. for 2 minutes; three cycles of 94 ° C. for 30 seconds, 64° C. for 30 seconds, 70° C. for 30 seconds; three cycles of 94° C. for 30 seconds, 58° C. for 30 seconds, 70° C. for 30 seconds; 35 cycles of 94° C. for 30 seconds, 57° C. for 30 seconds, and 70° C. for 30 seconds; and one cycle of 70° C. for 5 minutes. After the reaction was complete, the amplicons were purified using the AMPure PCR purification system (Agencourt Bioscience Corp.). The purified amplicons were sequenced using the BigDye® Terminator v.3.1 Cycle Sequencing Kit (Applied Biosystems) according to the manufacturer's instructions and analyzed with a 3730 ABI capillary electrophoresis system. Each exon sequence from the tumor DNA of a particular patient was compared to the wild-type exon sequence from normal DNA of that same patient to identify the presence of any mutations. The results of that analysis are shown in Table 2.

TABLE 2

Mutational Analysis of Certain EGFr, PI3K, and Ras Exons in CRC Patient Samples

| Patient | EGFr exon 18 | EGFr exon 19 | EGFr exon 21 | PI3K exon 9 | PI3K exon 20 | Ras exon 2 | B-Raf exon 15 |
|---|---|---|---|---|---|---|---|
| 1 - 30624793 | WT | WT | WT | WT | WT | WT | WT |
| 2 - 2350661 | WT | WT | WT | WT | WT | G13D | WT |
| 3 - 30640715 | WT | WT | WT | WT | WT | G12D | WT |
| 4 - 3039832 | WT | WT | WT | WT | WT | WT | WT |
| 5 - 10015851 | WT | WT | WT | WT | WT | G13D | WT |
| 6 - 30656334 | WT | WT | WT | WT | WT | G12V | WT |
| 7 - 30667900 | WT | WT | WT | WT | WT | WT | WT |
| 8 - 30384032 | WT | WT | WT | WT | WT | G13D | WT |
| 9 - 30692441 | WT | WT | WT | WT | WT | WT | WT |
| 10 - 30685324 | WT | WT | WT | WT | H1047R | WT | E599V |

The results in Tables 1 and 2 show that mutations in the EGFr catalytic domain (exons 18, 19, and 21), and mutations in Ras exon 1, PI3K exons 9 and 20, and mutations in B-Raf exon 15 were not correlated with efficacy of panitumumab treatment in the ten tested CRC patients.

Example 3

Analysis of EGFR Copy Number and Localization in CRC Tumor Samples

The number of copies of an EGFr gene in patient tumor samples was determined in two ways: by fluorescent in situ hybridization ("FISH") and by quantitative PCR. The FISH analysis was performed using the Her1 FISH detection kit (Dakocytomation, Denmark) according to the manufacturer's instructions. The kit permitted the differential fluorescent labeling of each EGFr gene, each chromosome 7 alpha-centromeric sequence ("CEP7"), and each nucleus present in the sample. Patient samples were placed in a pretreatment solution (provided in kit) for 30 minutes at 96° C. and subsequently digested with pepsin solution (provided in kit) for 30 minutes at room temperature. Dual-color, dual-target FISH assays were performed using the LSI EGFR Spectrum Orange probe (Vysis, Downers Grove, Ill.) and the CEP7 Spectrum Green probe (Vysis, Downers Grove, Ill.). Tissue sections were covered with 10 pL probe solution (provided in kit) and incubated at 75° C. for 5 minutes to co-denature the EGFr and CEP7 probes. The sections were allowed to hybridize overnight with the denatured probes at 37° C. The co-denaturation and hybridization steps were performed sequentially in a microprocessor-controlled system (Hybridizer, Dakocytomation, Denmark). After hybridization, the sections were washed twice at 65° C. for 10 minutes per wash using the wash buffer provided in the kit, and dried at room temperature for 15 minutes. The tissue sections were covered with 4'6-diamidino-2-phenylindole (DAPI II, Vysis) for chromatin counterstaining and examined by fluorescent microscopy.

A fluorescent microscope (Zeiss Axioskop, Germany) equipped with the Chromowin workstation (Amplimedical, Italy) was used for the FISH visualization. The EGFr gene was observed as a red signal with a tetramethyl-rhodamine isothiocyanate (TRITC) filter. The CEP7 sequence was observed as a green signal with a fluorescein isothiocyanate (FITC) filter. The cell nuclei were observed as a blue signal with a DAPI filter. Representative images of each specimen were taken with a Hamamatsu C5895 chilled CCD camera (Upstate Technical Equipment Co., New York) in monochromatic layers that were subsequently merged by Casti Imaging FISH Multicolor software (Amplimedical). Cultured retinal pigment epithelial cells and normal colorectal mucosal cells adjacent to the tumor cells in each patient sample were used as normal cell controls. A431 human epidermoid carcinoma cells were used as controls for increased EGFr gene copy number. The specimen from patient 5 was available only as a 10 micron section and despite multiple attempts, FISH analysis was not conclusive due to excessive tissue thickness.

Two independent observers scored at least 200 non-overlapping interphase nuclei from each sample using predefined scoring guidelines. The observers were blinded to both.the clinical characteristics of the patients and the scoring and assessment of the other observer. Within each nucleus, the number of copies of the EGFr gene and the CEP7 sequence were assessed independently. The ratio of the EGFr gene copy number to the number of nuclei (EGFr:nuclei) and the EGFr gene copy number to the CEP7 sequence number (EGFr:CEP7) were recorded. The results are shown in Table 3.

TABLE 3

Results of FISH Analysis of EGFr Gene Copy Number

| Patient | Response to panitumumab | EGFr gene:CEP7 | EGFr gene:nuclei |
|---|---|---|---|
| 1 - 30624793 | partial response | 2.50 | 4.80 |
| 2 - 2350661 | partial response | 2.13 | 6.80 |
| 3 - 30640715 | partial response | 3.27 | 8.20 |
| 4 - 3039832 | partial response | 1.19 | 3.38 |
| 5 - 10015851 | stable disease | n/a | n/a |
| 6 - 30656334 | stable disease | 1.04 | 1.88 |
| 7 - 30667900 | progressive disease | 0.91 | 1.70 |
| 8 - 30384032 | progressive disease | 1.02 | 2.00 |
| 9 - 30692441 | progressive disease | 1.03 | 2.00 |
| 10 - 30685324 | progressive disease | 1.18 | 2.10 |

An EGFr gene is normally located on chromosome 7, and thus the expected ratio of EGFr gene number:CEP7 sequence number was 1. The expected ratio of EGFr gene number:nuclei was 2, given that normally two copies of chromosome 7 would be present in the nucleus. An increased EGFr gene copy number can result from both chromosome 7 polysomy and from EGFr gene amplification. Normal disomy is thus indicated by an EGFr gene:CEP7 ratio of 1 and an EGFr gene:nuclei ratio of 2. Balanced polysomy is indicated by an EGFr gene:CEP7 ratio of 1 and an EGFr gene:nuclei ratio greater than 2. Normal disomy with amplification of an EGFr gene is indicated by an EGFr gene:CEP7 ratio of greater than 1 and an EGFr gene:nuclei ratio greater than 2. Increased EGFr gene copy number was arbitrarily defined as a value $\geq 3$ in the ratio of EGFr gene number:nucleus.

FIG. 1 shows certain dual-color FISH assay images, in which EGFr genes appear in red, and CEP7 sequences appear in green. FIG. 1A shows the staining pattern of normal colorectal mucosal cells, in which balanced disomy is observed. FIG. 1B shows the staining pattern of tumor cells from patient 7, also displaying balanced disomy. FIG. 1C shows the staining pattern of tumor cells from patient 4, displaying balanced polysomy. FIG. 1D shows the staining pattern of tumor cells from patient 1, displaying disomy with EGFr gene amplification.

The EGFr gene copy number is also determined for each patient using quantitative PCR. Real-time PCR is performed using an ABI PRISM® 7900HT apparatus and the SYBR® Green (Molecular Probes, Inc.) detection system (Applied Biosystems), following the manufacturer's instructions. The forward primer GAATTCGGATGCAGAGCTTC (SEQ ID NO: 22) and the reverse primer GACATGCTGCGGT-GTTTTC (SEQ ID NO: 23) are used to amplify a small (100-200 bp) non-repetitive region of an EGFr gene. Line-1, a repetitive element for which copy numbers per diploid genome are similar among all human cells, is also amplified from each patient sample to permit normalization of the EGFr gene results. The forward and reverse primers for the Line-1 repetitive element are AAAGCCGCTCAACTACATGG (SEQ ID NO: 24) and TGCTTTGAATGCGTCCCAGAG (SEQ ID NO: 25), respectively. The amplification conditions are as follows: one cycle of 10 minutes at 95° C. followed by 45 cycles of 15 seconds at 95°C. and 1 minute at 60° C. Threshold cycle numbers are obtained using the ABI PRISM® 7900HT Sequence Detection System software. Amplification reactions are performed in triplicate and threshold cycle numbers are averaged. Copy number. changes are calculated by using the formula $s^{(Dt-Dline)-(Nt-Nline)}$. In that formula, Dt is the average threshold cycle number observed for the EGFr gene sequence in a patient sample, Dline is the average threshold cycle number observed for the Line-1 sequence in a patient sample, Nt is the threshold cycle number observed for the EGFr gene sequence in DNA from retinal pigment epithelial cells ("RPE") cells, and Nline is the threshold cycle number observed for the Line-1 sequence in DNA from RPE cells.

Example 4

Cell Proliferation Inhibition Assay

Figure 2:
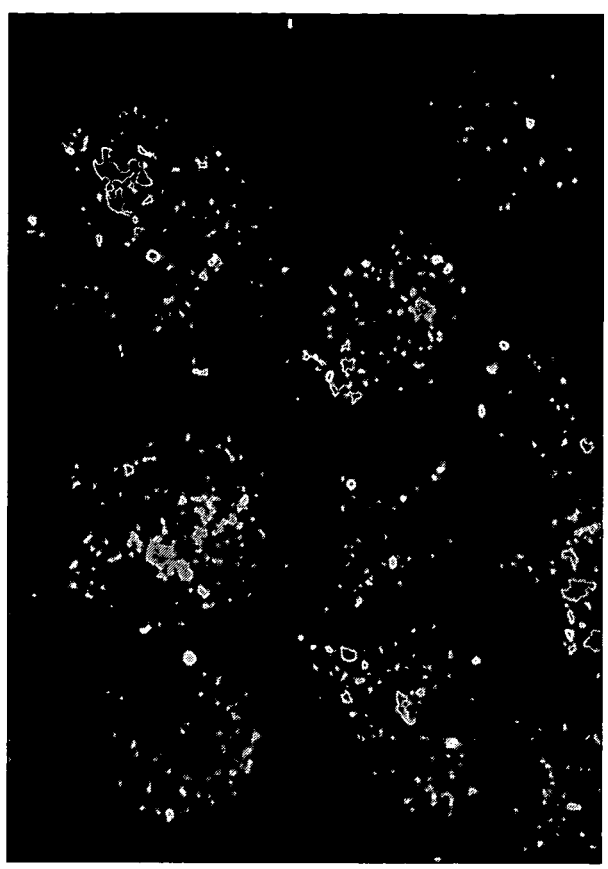
FIG. 2A is a Western blot showing the level of expression of EGFr in different colorectal carcinoma cell lines, according to work described in Example 4.
FIG. 2B is an image from a dual-color FISH assay analysis of DiFi colorectal carcinoma cells as seen by fluorescent microscope, according to work described in Example 4. EGFr genes appear red and CEP7 sequences appear green.
Figure 2:
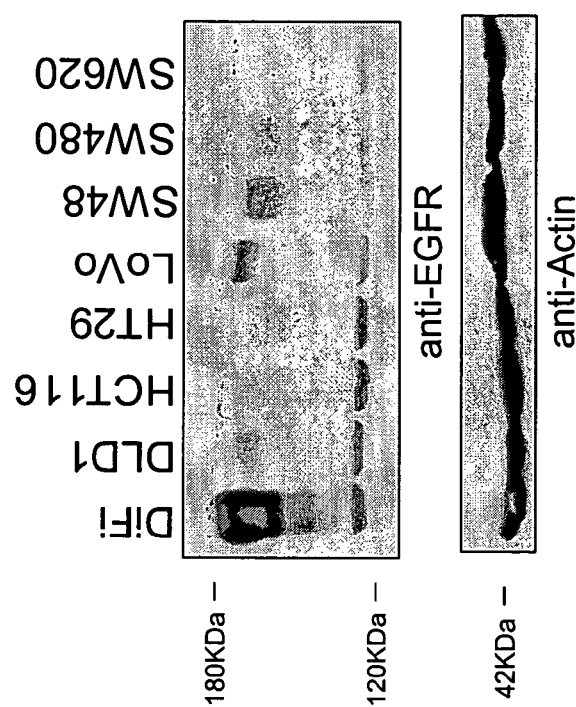

The effect of panitumumab on cell lines with a normal number of EGFr gene copies or with an increased number of EGFr gene copies are studied. First, the copy number of EGFr in experimental CRC cell lines was determined. Eight different CRC cell lines were studied: DiFi (Jose Baselga, Vall d'Hebron University, Barcelona, Spain), DLD-1, HCT-116, HT-29, LoVo, SW48, SW480, and SW620 (all from ATCC). The EGFr copy number of each CRC cell line was determined using the FISH methodology as described above in Example 3. Each cell line (with the exception of the DiFi cells) was grown in DMEM supplemented with 10% fetal calf serum, penicillin, and streptomycin. DiFi cells were grown in F-12 medium supplemented with 10% FCS and antibiotics. An exemplary FISH fluorescence stained image for DiFi cells is shown in FIG. 2B. The values obtained from the FISH analyses are shown in Table 4.

TABLE 4

Copy Number of EGFr Gene in CRC Cell Lines

| Cell Line | EGFr gene:CEP7 | EGFr gene:Nucleus |
|---|---|---|
| DiFi | >20 | >20 |
| SW48 | 1.10 | 3.19 |
| SW480 | 0.94 | 3.08 |
| SW620 | 1.05 | 3.00 |
| HT-29 | 0.97 | 2.52 |
| LoVo | 0.98 | 2.41 |
| HCT-116 | 0.93 | 1.79 |
| DLD-1 | 0.93 | 1.68 |

As shown in Table 4, DiFi cells have a very high EGFr gene copy number.

EGFr gene expression was examined in each of the cell lines by Western blot analysis of cellular EGFr protein (see FIG. 2A). Protein extracts were subjected to electrophoresis via SDS-PAGE and transferred to polyvinylidene difluoride membranes by high-intensity wet blotting. Filters were probed with the indicated antibodies, and specific binding was detected using an enhanced chemiluminescence system (Amersham). As expected from the FISH data, above, DiFi cells had a very high level of EGFr protein. With the exception of SW620, the other cell lines showed variable levels of EGFr protein. SW260 cells did not contain EGFr protein, despite a high EGFr gene copy number.

The effect of panitumumab on proliferation of each of the CRC tumor cell lines is measured using a bromodeoxyuridine ("BrdU") incorporation assay. Cells are grown in DMEM supplemented with 2% FBS in 96-well black plates (Culture Plate™ 96F (Packard Bioscience)). The plated cells are incubated for 5 days with varying concentrations between 0.01-100 nM panitumumab (Amgen Inc.). Cell proliferation is measured by a chemiluminscent ELISA method assaying BrdU incorporation (Roche). The cell seeding density per well for each cell line is as follows: DiFi: 4000; LoVo: 4000; DLD: 500; HCT116: 1000; HT29: 1000; SW480: 1000; SW387: 4000; SW48: 500; and SW620: 500. The BrdU assay is performed in three separate triplicate experiments according to the manufacturer's instructions and is terminated 20 hours after addition of the labeling solution. The percentage of cell proliferation at each panitumumab concentration is calculated using the following formula: [(test sample−blank sample)/(control sample−blank sample)×100], where the control sample is cells grown in medium lacking panitumumab, and the blank sample consists of cells grown in 0.02% Triton X in DMEM (i.e., no growth).

We claim:

1. A method of predicting whether an anti-EGFr antibody will be efficacious in treating colorectal cancer in a subject, comprising determining the EGFr gene copy number in a colorectal sample from the subject, wherein the presence of an increased EGFr gene copy number in the sample predicts that an anti-EGFr antibody will be efficacious in treating colorectal cancer in the subject.

2. The method of claim 1, wherein the anti-EGFr antibody is a human anti-EGFr antibody.

3. The method of claim 2, wherein the human anti-EGFr antibody is panitumumab.

4. The method of claim 1, wherein determining the EGFr gene copy number in the sample comprises comparing the EGFr gene copy number in the sample to the EGFr gene copy number in a normal reference sample.

5. The method of claim 4, wherein determining the EGFr gene copy number comprises fluorescent in situ hybridization analysis.

6. The method of claim 4, wherein determining the EGFr gene copy number comprises quantitative PCR analysis.

7. The method of claim 4, wherein determining the EGFr gene copy number comprises Southern blot analysis.

8. The method of claim 1, wherein determining the EGFr gene copy number comprises:

(a) determining the EGFr gene copy number in a test sample from a tumor in the subject;

(b) determining the copy number of at least one reference nucleotide sequence in the test sample; and (c) comparing the EGFr gene copy number to the at least one reference nucleotide sequence copy number, wherein an increased copy number of the EGFr gene in the test sample relative to the copy number of the at least one reference nucleotide sequence predicts that an anti-EGFr antibody will be efficacious in treating colorectal cancer in the subject.

9. The method of claim 8, wherein the at least one reference nucleotide sequence copy number is two copies per cell.

10. The method of claim 8, wherein the at least one reference nucleotide sequence is a centromeric sequence.

11. The method of claim 8, wherein determining the EGFr gene copy number and the at least one reference nucleotide sequence copy number comprises fluorescent in situ hybridization analysis.

12. The method of claim 8, wherein determining the EGFr gene copy number and the at least one reference nucleotide sequence copy number comprises quantitative PCR analysis.

13. The method of claim 8, wherein determining the EGFr gene copy number and the at least one reference nucleotide sequence copy number comprises Southern blot analysis.

14. The method of claim 8, wherein the anti-EGFr antibody is a human anti-EGFr antibody.

15. The method of claim 14, wherein the human anti-EGFr antibody is panitumumab.

16. The method of claim 1, wherein determining the EGFr gene copy number comprises:
(a) determining the EGFr gene copy number in a test sample from the subject;
(b) determining the number of nuclei in the test sample; and
(c) comparing the EGFr gene copy number to the number of nuclei, wherein a ratio greater than two predicts that an anti-EGFr antibody will be efficacious in treating colorectal cancer in the subject.

17. The method of claim 16, wherein determining the EGFr gene copy number and the number of nuclei comprises fluorescent in situ hybridization analysis.

18. The method of claim 16, wherein the anti-EGFr antibody is a human anti-EGFr antibody.

19. The method of claim 18, wherein the human anti-EGFr antibody is panitumumab.

* * * * *

UNITED STATES PATENT AND TRADEMARK OFFICE
CERTIFICATE OF CORRECTION

| | | |
|---|---|---|
| PATENT NO. | : 7,635,570 B2 | Page 1 of 1 |
| APPLICATION NO. | : 11/396311 | |
| DATED | : December 22, 2009 | |
| INVENTOR(S) | : Siena et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 170 days.

Signed and Sealed this

Ninth Day of November, 2010

David J. Kappos
*Director of the United States Patent and Trademark Office*

SEQUENCE LISTING

<160> NUMBER OF SEQ ID NOS: 25

<210> SEQ ID NO 1
<211> LENGTH: 20
<212> TYPE: DNA
<213> ORGANISM: Artificial

```
<220> FEATURE:
<223> OTHER INFORMATION: oligonucleotide primer

<400> SEQUENCE: 1
gctgaggtga cccttgtctc                                               20

<210> SEQ ID NO 2
<211> LENGTH: 20
<212> TYPE: DNA
<213> ORGANISM: Artificial
<220> FEATURE:
<223> OTHER INFORMATION: oligonucleotide primer

<400> SEQUENCE: 2
acagcttgca aggactctgg                                               20

<210> SEQ ID NO 3
<211> LENGTH: 20
<212> TYPE: DNA
<213> ORGANISM: Artificial
<220> FEATURE:
<223> OTHER INFORMATION: oligonucleotide primer

<400> SEQUENCE: 3
tggagcctct tacacccagt                                               20

<210> SEQ ID NO 4
<211> LENGTH: 19
<212> TYPE: DNA
<213> ORGANISM: Artificial
<220> FEATURE:
<223> OTHER INFORMATION: oligonucleotide primer

<400> SEQUENCE: 4
cccagtgtcc ctcaccttc                                                19

<210> SEQ ID NO 5
<211> LENGTH: 20
<212> TYPE: DNA
<213> ORGANISM: Artificial
<220> FEATURE:
<223> OTHER INFORMATION: oligonucleotide primer

<400> SEQUENCE: 5
ccacacagca aagcagaaac                                               20

<210> SEQ ID NO 6
<211> LENGTH: 20
<212> TYPE: DNA
<213> ORGANISM: Artificial
<220> FEATURE:
<223> OTHER INFORMATION: oligonucleotide primer

<400> SEQUENCE: 6
gctggtaaca tccacccaga                                               20

<210> SEQ ID NO 7
<211> LENGTH: 20
<212> TYPE: DNA
<213> ORGANISM: Artificial
<220> FEATURE:
<223> OTHER INFORMATION: oligonucleotide primer

<400> SEQUENCE: 7
tgatctgtcc ctcacagcag                                               20
```

```
<210> SEQ ID NO 8
<211> LENGTH: 20
<212> TYPE: DNA
<213> ORGANISM: Artificial
<220> FEATURE:
<223> OTHER INFORMATION: oligonucleotide primer

<400> SEQUENCE: 8
tcaggaaaat gctggctgac                                               20

<210> SEQ ID NO 9
<211> LENGTH: 21
<212> TYPE: DNA
<213> ORGANISM: Artificial
<220> FEATURE:
<223> OTHER INFORMATION: oligonucleotide primer

<400> SEQUENCE: 9
ttcagggcat gaactacttg g                                             21

<210> SEQ ID NO 10
<211> LENGTH: 23
<212> TYPE: DNA
<213> ORGANISM: Artificial
<220> FEATURE:
<223> OTHER INFORMATION: oligonucleotide primer

<400> SEQUENCE: 10
gggaaaaata tgacaaagaa agc                                           23

<210> SEQ ID NO 11
<211> LENGTH: 22
<212> TYPE: DNA
<213> ORGANISM: Artificial
<220> FEATURE:
<223> OTHER INFORMATION: oligonucleotide primer

<400> SEQUENCE: 11
ctgagatcag ccaaattcag tt                                            22

<210> SEQ ID NO 12
<211> LENGTH: 27
<212> TYPE: DNA
<213> ORGANISM: Artificial
<220> FEATURE:
<223> OTHER INFORMATION: oligonucleotide primer

<400> SEQUENCE: 12
tagctagaga caatgaatta agggaaa                                       27

<210> SEQ ID NO 13
<211> LENGTH: 20
<212> TYPE: DNA
<213> ORGANISM: Artificial
<220> FEATURE:
<223> OTHER INFORMATION: oligonucleotide primer

<400> SEQUENCE: 13
ctcaatgatg cttggctctg                                               20

<210> SEQ ID NO 14
<211> LENGTH: 21
<212> TYPE: DNA
<213> ORGANISM: Artificial
<220> FEATURE:
<223> OTHER INFORMATION: oligonucleotide primer
```

```
<400> SEQUENCE: 14
tggaatccag agtgagcttt c                                            21

<210> SEQ ID NO 15
<211> LENGTH: 22
<212> TYPE: DNA
<213> ORGANISM: Artificial
<220> FEATURE:
<223> OTHER INFORMATION: oligonucleotide primer

<400> SEQUENCE: 15
ttgatgacat tgcatacatt cg                                           22

<210> SEQ ID NO 16
<211> LENGTH: 26
<212> TYPE: DNA
<213> ORGANISM: Artificial
<220> FEATURE:
<223> OTHER INFORMATION: oligonucleotide primer

<400> SEQUENCE: 16
ggtggagtat ttgatagtgt attaac                                       26

<210> SEQ ID NO 17
<211> LENGTH: 21
<212> TYPE: DNA
<213> ORGANISM: Artificial
<220> FEATURE:
<223> OTHER INFORMATION: oligonucleotide primer

<400> SEQUENCE: 17
agaatggtcc tgcaccagta a                                            21

<210> SEQ ID NO 18
<211> LENGTH: 27
<212> TYPE: DNA
<213> ORGANISM: Artificial
<220> FEATURE:
<223> OTHER INFORMATION: oligonucleotide primer

<400> SEQUENCE: 18
tcattatttt tattataagg cctgctg                                      27

<210> SEQ ID NO 19
<211> LENGTH: 22
<212> TYPE: DNA
<213> ORGANISM: Artificial
<220> FEATURE:
<223> OTHER INFORMATION: oligonucleotide primer

<400> SEQUENCE: 19
tgcttgctct gataggaaaa tg                                           22

<210> SEQ ID NO 20
<211> LENGTH: 20
<212> TYPE: DNA
<213> ORGANISM: Artificial
<220> FEATURE:
<223> OTHER INFORMATION: oligonucleotide primer

<400> SEQUENCE: 20
agcatctcag ggccaaaaat                                              20
```

```
<210> SEQ ID NO 21
<211> LENGTH: 26
<212> TYPE: DNA
<213> ORGANISM: Artificial
<220> FEATURE:
<223> OTHER INFORMATION: oligonucleotide primer

<400> SEQUENCE: 21
tgttttcctt tacttactac acctca                                          26

<210> SEQ ID NO 22
<211> LENGTH: 20
<212> TYPE: DNA
<213> ORGANISM: Artificial
<220> FEATURE:
<223> OTHER INFORMATION: oligonucleotide primer

<400> SEQUENCE: 22
gaattcggat gcagagcttc                                                 20

<210> SEQ ID NO 23
<211> LENGTH: 19
<212> TYPE: DNA
<213> ORGANISM: Artificial
<220> FEATURE:
<223> OTHER INFORMATION: oligonucleotide primer

<400> SEQUENCE: 23
gacatgctgc ggtgttttc                                                  19

<210> SEQ ID NO 24
<211> LENGTH: 20
<212> TYPE: DNA
<213> ORGANISM: Artificial
<220> FEATURE:
<223> OTHER INFORMATION: oligonucleotide primer

<400> SEQUENCE: 24
aaagccgctc aactacatgg                                                 20

<210> SEQ ID NO 25
<211> LENGTH: 21
<212> TYPE: DNA
<213> ORGANISM: Artificial
<220> FEATURE:
<223> OTHER INFORMATION: oligonucleotide primer

<400> SEQUENCE: 25
tgctttgaat gcgtcccaga g                                               21
```